(12) United States Patent
Varner et al.

(10) Patent No.: US 8,808,698 B2
(45) Date of Patent: Aug. 19, 2014

(54) METHODS FOR INHIBITION OF LYMPHANGIOGENESIS AND TUMOR METASTASIS

(75) Inventors: Judith Varner, Encinitas, CA (US); Barbara Garmy-Susini, Encintas, CA (US)

(73) Assignee: The Regents of the University of California, Oakland, CA (US)

( * ) Notice: Subject to any disclaimer, the term of this patent is extended or adjusted under 35 U.S.C. 154(b) by 1170 days.

(21) Appl. No.: 12/223,380

(22) PCT Filed: Feb. 5, 2007

(86) PCT No.: PCT/US2007/003205
§ 371 (c)(1),
(2), (4) Date: Dec. 16, 2008

(87) PCT Pub. No.: WO2007/092471
PCT Pub. Date: Aug. 16, 2007

(65) Prior Publication Data
US 2010/0055089 A1    Mar. 4, 2010

Related U.S. Application Data

(60) Provisional application No. 60/765,068, filed on Feb. 3, 2006.

(51) Int. Cl.
| | | |
|---|---|---|
| *A61K 31/00* | (2006.01) | |
| *A61K 38/00* | (2006.01) | |
| *A61K 39/395* | (2006.01) | |
| *A61K 49/00* | (2006.01) | |

(52) U.S. Cl.
USPC .......... 424/137.1; 424/9.1; 424/130.1; 514/1; 514/1.1; 514/13.1; 514/19.2; 514/19.3; 514/19.8

(58) Field of Classification Search
CPC ..... A61K 31/00; A61K 38/00; A61K 39/395; A61K 49/00; A01N 61/00
USPC ........... 424/9.1, 130.1; 514/1, 1.1, 13.1, 19.2, 514/19.3, 19.8
See application file for complete search history.

(56) References Cited

U.S. PATENT DOCUMENTS

| | | | | |
|---|---|---|---|---|
| 4,244,946 | A |  1/1981 | Rivier et al. | 514/9.9 |
| 5,225,347 | A |  7/1993 | Goldberg et al. | 435/320.1 |
| 5,246,921 | A |  9/1993 | Reddy et al. | 514/44 R |
| 5,500,357 | A |  3/1996 | Taira et al. | 435/91.31 |
| 5,527,895 | A |  6/1996 | Hampel et al. | 536/23.2 |
| 5,750,105 | A |  5/1998 | Newman et al. | 424/133.1 |
| 5,780,426 | A |  7/1998 | Palladino et al. | 514/13.3 |
| 5,795,715 | A |  8/1998 | Livache et al. | 435/6.18 |
| 6,252,043 | B1 |  6/2001 | Hession et al. | 530/350 |
| 7,824,680 | B2 * | 11/2010 | Varner | 424/143.1 |

FOREIGN PATENT DOCUMENTS

| | | |
|---|---|---|
| EP | 0140308 B1 | 1/1993 |
| EP | 0842943 B1 | 2/2003 |
| WO | WO/92/00995 | 1/1991 |
| WO | WO/95/14714 | 6/1995 |
| WO | WO/95/15973 | 6/1995 |
| WO | WO/96/00581 | 1/1996 |
| WO | WO/96/02644 | 2/1996 |
| WO | WO/96/06108 | 2/1996 |
| WO | WO/96/20216 | 7/1996 |
| WO | WO/96/22966 | 8/1996 |
| WO | WO/97/02289 | 1/1997 |
| WO | WO/98/42656 | 10/1998 |
| WO | WO 02/18320 A2 * | 3/2002 |
| WO | WO/03/19136 | 3/2003 |
| WO | WO 03/019136 A2 * | 3/2003 |
| WO | PCT/US2007/003205 | 8/2007 |

OTHER PUBLICATIONS

Taswell et al. (The Journal of Bone and Joint Surgery 44A(2): 277-294, Mar. 1962).*
U.S. Appl. No. 60/765,068, filed Feb. 3, 2006, Varner, J. and Garmy-susini, B.
Achen, M. G. et al. (2000) Monoclonal antibodies to vascular endothelial growth factor-D block its interactions with both VEGF receptor-2 and VEGF receptor-3, *European Journal of Biochemistry*267(9), 2505-2515.
Achen, M. G. And Stacker, S. A. (1998) The vascular endothelial growth factor family; proteins which guide the development of the vasculature, *International Journal of Experimental Pathology*79(5), 255-265.
Alitalo, K. et al. (2005) Lymphangiogenesis in development and human disease, *Nature*438(7070), 946-953.
Asahara, T. et al. (1995) Synergistic Effect of Vascular Endothelial Growth Factor and Basic Fibroblast Growth Factor on Angiogenesis in Vivo, *Circulation*92(9), 365-371.
Atherton, E. et al. (1985) Peptide synthesis. Part 7. Solid-phase synthesis of conotoxin G1, *Journal of the Chemical Society, Perkin Transactions*1, 2065-2073.
Bakre, M. M. et al. (2002) Parathyroid hormone-related peptide is a naturally occurring, protein kinase A-dependent angiogenesis inhibitor, *Nature Medicine*8(9), 995-1003.
Banerji, S. et al. (1999) LYVE-1, a New Homologue of the CD44 Glycoprotein, Is a Lymph-specific Receptor for Hyaluronan,*The Journal of Cell Biology*144(4), 789-801.

(Continued)

*Primary Examiner* — Alana Harris Dent
(74) *Attorney, Agent, or Firm* — Medlen & Carroll, LLP

(57) ABSTRACT

The present invention is directed to compositions and methods for inhibiting the development of new lymphatic vessels, and for inhibiting tumor cell dissemination through the lymphatics. In preferred embodiments, the present invention utilizes agents that inhibit the specific binding of integrin alpha4beta1 ($\alpha 4\beta 1$, VLA-4) to one or more of its ligands. The invention further relates to methods for screening test compounds for their ability to inhibit undesirable lymphangiogenesis and/or tumor metastasis.

5 Claims, 35 Drawing Sheets

(56) References Cited

OTHER PUBLICATIONS

Bochner, B. S. et al. (1991) Adhesion of human basophils, eosinophils, and neutrophils to interleukin 1-activated human vascular endothelial cells: contributions of endothelial cell adhesion molecules, *The Journal of Experimental Medicine* 173(6), 1553-1557.

Brando, C. et al. (2000) EC3, a Heterodimeric Disintegrin from Echis carinatus, Inhibits Human and Murine α4 Integrin and Attenuates Lymphocyte Infiltration of Langerhans Islets in Pancreas and Salivary Glands in Nonobese Diabetic Mice, *Biochemical and Biophysical Research Communications* 267(1), 413-417.

Breiteneder-Geleff, S. et al. (1999) Angiosarcomas Express Mixed Endothelial Phenotypes of Blood and Lymphatic Capillaries Podoplanin as a Specific Marker for Lymphatic Endothelium, *The American Journal of Pathology* 154(2), 385-394.

Cardarelli, P. M. et al. (1994) Cyclic RGD peptide inhibits alpha 4 beta 1 interaction with connecting segment 1 and vascular cell adhesion molecule, *Journal of Biological Chemistry* 269(28), 18668-18673.

Carlsson, R. et al. (1989) Monoclonal Antibodies into the '90s: The All-Purpose Tool, *Bio/Technology* 7(6), 567-573.

Carmeliet, P. (2003) Angiogenesis in health and disease, *Nature Medicine* 9(6), 653-660.

Carthew, R. W. (2001) Gene silencing by double-stranded RNA, *Current Opinion in Cell Biology* 13(2), 244-248.

Casley Smith, J. R. (1980) The fine structure and functioning of tissue channels and lymphatics, *Lymphology* 13(4), 177-183.

Chisholm, P. L. et al. (1993) Monoclonal antibodies to the integrin α-4 subunit inhibit the murine contact hypersensitivity response, *European Journal of Immunology* 23(3), 682-688.

Clements, J. M. et al. (1994) Identification of a key integrin-binding sequence in VCAM-1 homologous to the LDV active site in fibronectin, *Journal of Cell Science* 107(8), 2127-2135.

Curley, G. P. et al. (1999) Integrin antagonists, *Cellular and Molecular Life Sciences* 56(5), 427-441.

Cursiefen, C. et al. (2004) VEGF-A stimulates lymphangiogenesis and hemangiogenesis in inflammatory neovascularization via macrophage recruitment, *Journal of Clinical Investigation* 113(7), 1040-1050.

Dittel, B. et al. (1993) Regulation of human B-cell precursor adhesion to bone marrow stromal cells by cytokines that exert opposing effects on the expression of vascular cell adhesion molecule-1 (VCAM-1), *Blood* 81(9), 2272-2282.

Dudgeon, T. J. et al. (1994) Expression and Characterization of a Very-Late Antigen-4 (α4β1) Integrin-Binding Fragment of Vascular Cell-Adhesion Molecule-1, *European Journal of Biochemistry* 226(2), 517-523.

Eliceiri, B. P. et al. (1999) Selective Requirement for Src Kinases during VEGF-Induced Angiogenesis and Vascular Permeability, *Molecular Cell* 4(6), 915-924.

Fields, G. B. and Noble, R. L. (1990) Solid phase peptide synthesis utilizing 9-fluorenylmethoxycarbonyl amino acids, *International Journal of Peptide & Protein Research* 35(3), 161-214.

Fire, A. et al. (1998) Potent and specific genetic interference by double-stranded RNA in Caenorhabditis elegans, *Nature* 391(6669), 806.

Garcia-Pardo, A. et al. (1992) Two novel monoclonal antibodies to fibronectin that recognize the hep II and CS-1 regions respectively: Their differential effect on lymphocyte adhesion, *Biochemical and Biophysical Research Communications* 186(1), 135-142.

Garmy-Susini, B. et al. (2005) Integrin alpha4beta1-VCAM-1-mediated adhesion between endothelial and mural cells is required for blood vessel maturation, *Journal of Clinical Investigation* 115(6), 1542-1551.

Goto, F. et al. (1993) Synergistic effects of vascular endothelial growth factor and basic fibroblast growth factor on the proliferation and cord formation of bovine capillary endothelial cells within collagen gels, *Laboratory Investigation* 69(5), 508-517.

Guerrier-Takada, C. et al. (1983) The RNA moiety of ribonuclease P is the catalytic subunit of the enzyme, *Cell* 35(3, Part 2), 849-857.

Guo, S. And Kemphues, K. J. (1995) par-1, a gene required for establishing polarity in C. elegans embryos, encodes a putative Ser/Thr kinase that is asymmetrically distributed, *Cell* 81(4), 611-620.

Hambor, J. E. et al. (1988) Functional consequences of anti-sense RNA-mediated inhibition of CD8 surface expression in a human T cell clone, *The Journal of Experimental Medicine* 168(4), 1237-1245.

Hemler, M. E. et al. (1987) The VLA protein family. Characterization of five distinct cell surface heterodimers each with a common 130,000 molecular weight beta subunit, *Journal of Biological Chemistry* 262(7), 3300-3309.

Hemler, M. E. et al. (1987) Characterization of the cell surface heterodimer VLA-4 and related peptides, *Journal of Biological Chemistry* 262(24), 11478-11485.

Hofacker, I. L. et al. (1994) Fast Folding and Comparison of RNA Secondary Structures, *Monatshefte Fur Chemie* 125, 167-188.

Holzmann, B. et al. (1989) Identification of a murine Peyer's patch—specific lymphocyte homing receptor as an integrin molecule with an α chain homologous to human VLA-4α, *Cell* 56(1), 37-46.

Hood, J. D. and Cheresh, D. A. (2002) Role of integrins in cell invasion and migration, *Nature Reviews Cancer* 2(2), 91-100.

Huang, X. Z. et al. (2000) Fatal Bilateral Chylothorax in Mice Lacking the Integrin α9β1, *Molecular and Cellular Biology* 20(14), 5208-5215.

Humphries, M. J. et al. (1986) A Synthetic Peptide from Fibronectin Inhibits Experimental Metastasis of Murine Melanoma Cells, *Science* 233(4762), 467-470.

Humphries, M. J. et al. (1988) Investigation of the biological effects of anti-cell adhesive synthetic peptides that inhibit experimental metastasis of B16-F10 murine melanoma cells, *Journal of Clinical Investigation* 81(3), 782-790.

Huse, W. D. et al. (1989) Generation of a large combinatorial library of the immunoglobulin repertoire in phage lambda, *Science* 246(4935), 1275-1281.

Issekutz, T. B. (1991) Inhibition of in vivo lymphocyte migration to inflammation and homing to lymphoid tissues by the TA-2 monoclonal antibody. A likely role for VLA-4 in vivo, *The Journal of Immunology* 147(12), 4178-4184.

Jackson, D. Y. et al. (1997) Potent α4β1 Peptide Antagonists as Potential Anti-Inflammatory Agents, *Journal of Medicinal Chemistry* 40(21), 3359-3368.

Joukov, V. et al. (1996) A novel vascular endothelial growth factor, VEGF-C, is a ligand for the Flt4 (VEGFR-3) and KDR (VEGFR-2) receptor tyrosine kinases, *The EMBO Journal* 15(7), 1751.

Kaipainen, A. et al. (1995) Expression of the fms-like tyrosine kinase 4 gene becomes restricted to lymphatic endothelium during development, *Proceedings of the National Academy of Sciences* 92(8), 3566-3570.

Kamber, B. et al. (1980) The Synthesis of Cystine Peptides by Iodine Oxidation of S-Trityl-cysteine and S-Acetamidomethyl-cysteine Peptides, *Helvetica Chimica Acta* 63(4), 899-915.

Karkkainen, M. J. et al. (2002) Lymphatic endothelium: a new frontier of metastasis research, *Nature Cell Biology* 4(1), E2-E5.

Kennedy, R. C. et al. (1986) Anti-idiotypes and immunity, *Scientific American* 255(1), 48-56.

Kim, S. et al. (2002) Inhibition of endothelial cell survival and angiogenesis by protein kinase A, *Journal of Clinical Investigation* 110(7), 933-941.

Kim, S. et al. (2000) Regulation of Integrin αvβ3-mediated Endothelial Cell Migration and Angiogenesis by Integrin α5β1 and Protein Kinase A, *Journal of Biological Chemistry* 275(43), 33920-33928.

Kinashi, T. and Springer, T. A. (1994) Adhesion molecules in hematopoietic cells, *Blood Cells* 20(1), 25-44.

Koivunen, E. et al. (1994) Isolation of a highly specific ligand for the alpha 5 beta 1 integrin from a phage display library, *The Journal of Cell Biology* 124(3), 373-380.

Kruger, K. et al. (1982) Self-splicing RNA: Autoexcision and autocyclization of the ribosomal RNA intervening sequence of tetrahymena, *Cell* 31(1), 147-157.

Lin, K.-c. et al. (1999) Selective, Tight-Binding Inhibitors of Integrin α4β1 That Inhibit Allergic Airway Responses, *Journal of Medicinal Chemistry* 42(5), 920-934.

(56) References Cited

OTHER PUBLICATIONS

Lin, K.-C. And Castro, A. C. (1998) Very late antigen 4 (VLA4) antagonists as anti-inflammatory agents, *Current Opinion in Chemical Biology* 2(4), 453-457.
Lohela, M. et al. (2003) Lymphangiogenic growth factors, receptors and therapies, *Thrombosis and Haemostasis* 90(2), 167-184.
Makinen, T. et al. (2001) Isolated lymphatic endothelial cells transduce growth, survival and migratory signals via the VEGFC/D receptor VEGFR-3, *The EMBO Journal* 20(17), 4762-4773.
Mancardi, S. et al. (1999) Lymphatic Endothelial Tumors Induced by Intraperitoneal Injection of Incomplete Freund's Adjuvant, *Experimental Cell Research* 246(2), 368-375.
Marcinkiewicz, C. et al. (1999) EC3, a Novel Heterodimeric Disintegrin from Echis carinatus Venom, Inhibits $\alpha 4$ and $\alpha 5$ Integrins in an RGD-independent Manner, *Journal of Biological Chemistry* 274(18), 12468-12473.
Marcus-Sekura, C. J. (1988) Techniques for using antisense oligodeoxyribonucleotides to study gene expression, *Analytical Biochemistry* 172(2), 289-295.
McCaskill, J. S. (1990) The equilibrium partition function and base pair binding probabilities for RNA secondary structure, *Biopolymers* 29(6-7), 1105-1119.
Merrifield, R. B. (1969) Solid-phase peptide synthesis, *Advances in enzymology and related subjects* 32, 221-296.
Miyake, K. et al. (1992) Requirement for VLA-4 and VLA-5 integrins in lymphoma cells binding to and migration beneath stromal cells in culture, *The Journal of Cell Biology* 119(3), 653-662.
Mostafavi-Pour, Z. et al. (2001) Identification of a novel heparin-binding site in the alternatively spliced IIICS region of fibronectin: roles of integrins and proteoglycans in cell adhesion to fibronectin splice variants, *Matrix Biology* 20(1), 63-73.
Muñoz, M. et al. (1997) A novel region of the alpha4 integrin subunit with a modulatory role in VLA-4-mediated cell adhesion to fibronectin, *Biochemical Journal* 327(3), 727-733.
Needham, A. et al. (1994) Activation dependent and independent VLA-4 binding sites on vascular cell adhesion molecule-1, *Cell Adhesion & Communication* 2(2), 87-99.
Nowlin, D. M. et al. (1993) A novel cyclic pentapeptide inhibits alpha 4 beta 1 and alpha 5 beta 1 integrin-mediated cell adhesion, *Journal of Biological Chemistry* 268(27), 20352-20359.
Pepper, M. S. et al. (1992) Potent synergism between vascular endothelial growth factor and basic fibroblast growth factor in the induction of angiogenesis in vitro, *Biochemical and Biophysical Research Communications* 189(2), 824-831.
Pepper, M. S. et al. (1998) Vascular endothelial growth factor (VEGF)-C synergizes with basic fibroblast growth factor and VEGF in the induction of angiogenesis in vitro and alters endothelial cell extracellular proteolytic activity, *Journal of Cellular Physiology* 177(3), 439-452.
Plaué, S. (1990) Synthesis of cyclic peptides on solid support. Application to analogs of hemagglutinin of influenza virus, *International Journal of Peptide & Protein Research* 35(6), 510-517.
Prevo, R. et al. (2001) Mouse LYVE-1 Is an Endocytic Receptor for Hyaluronan in Lymphatic Endothelium, *Journal of Biological Chemistry* 276(22), 19420-19430.
Puttaraju, M. et al. (1993) A circular trans-acting hepatitis delta virus ribozyme, *Nucleic Acids Research* 21(18), 4253-4258.
Quackenbush, E. J. And Letarte, M. (1985) Identification of several cell surface proteins of non-T, non-B acute lymphoblastic leukemia by using monoclonal antibodies, *The Journal of Immunology* 134(2), 1276-1285.
Rose, D. M. et al. (2000) Soluble VCAM-1 binding to $\alpha 4$ integrins is cell-type specific and activation dependent and is disrupted during apoptosis in T cells, *Blood* 95(2), 602-609.
Saaristo, A. et al. (2000) Mechanisms of angiogenesis and their use in the inhibition of tumor growth and metastasis, *Oncogene* 19(53), 6122-6129.
Sánchez-Madrid, F. et al. (1986) VLA-3: A novel polypeptide association within the VLA molecular complex: cell distribution and biochemical characterization, *European Journal of Immunology* 16(11), 1343-1349.
Schoppmann, S. F. et al. (2002) Tumor-Associated Macrophages Express Lymphatic Endothelial Growth Factors and Are Related to Peritumoral Lymphangiogenesis, *The American Journal of Pathology* 161(3), 947-956.
Sheremata, W. A. et al. (1999) A safety and pharmacokinetic study of intravenous natalizumab in patients with MS, *Neurology* 52(5), 1072-1074.
Sioud, M. And Drlica, K. (1991) Prevention of human immunodeficiency virus type 1 integrase expression in *Escherichia coli* by a ribozyme, *Proceedings of the National Academy of Sciences* 88(16), 7303-7307.
Souers, A. J. et al. (1998) Novel inhibitors of $\alpha 4\beta 1$ integrin receptor interactions through library synthesis and screening, *Bioorganic & Medicinal Chemistry Letters* 8(17), 2297-2302.
Stacker, S. A. et al. (2002) Metastasis: Lymphangiogenesis and cancer metastasis, *Nature Reviews Cancer* 2(8), 573-583.
Strömblad, S. And Cheresh, D. A. (1996) Cell adhesion and angiogenesis, *Trends in Cell Biology* 6(12), 462-468.
Tam, J. P. et al. (1991) Disulfide bond formation in peptides by dimethyl sulfoxide. Scope and applications, *Journal of the American Chemical Society* 113(17), 6657-6662.
Thomas, C. E. et al. (2003) Progress and problems with the use of viral vectors for gene therapy, *Nature Reviews Genetics* 4(5), 346-358.
Tubridy, N. et al. (1999) The effect of anti-alpha4 integrin antibody on brain lesion activity in MS, *Neurology* 53(3), 466-472.
Vauthier, C. et al. (2003) Poly(alkylcyanoacrylates) as biodegradable materials for biomedical applications, *Advanced Drug Delivery Reviews* 55(4), 519-548.
Vlahakis, N. E. et al. (2005) The Lymphangiogenic Vascular Endothelial Growth Factors VEGF-C and -D Are Ligands for the Integrin $\alpha 9\beta 1$, *Journal of Biological Chemistry* 280(6), 4544-4552.
Ward, E. S. et al. (1989) Binding activities of a repertoire of single immunoglobulin variable domains secreted from *Escherichia coli*, *Nature* 341(6242), 544-546.
Wayner, E. A. et al. (1989) Identification and characterization of the T lymphocyte adhesion receptor for an alternative cell attachment domain (CS-1) in plasma fibronectin, *The Journal of Cell Biology* 109(3), 1321-1330.
Wayner, E. A. And Kovach, N. L. (1992) Activation-dependent recognition by hematopoietic cells of the LDV sequence in the V region of fibronectin, *The Journal of Cell Biology* 116(2), 489-497.
Wigle, J. T. And Oliver, G. (1999) Prox1 Function Is Required for the Development of the Murine Lymphatic System, *Cell* 98(6), 769-778.
Winter, G. And Harris, W. J. (1993) Humanized antibodies, *Immunology Today* 14(6), 243-246.
Wu, H.-N. and Lai, M. M. C. (1989) Reversible Cleavage and Ligation of Hepatitis Delta Virus RNA, *Science* 243(4891), 652-654.
Yednock, T. A. et al. (1995) $\alpha 4\beta 1$ Integrin-dependent Cell Adhesion Is Regulated by a Low Affinity Receptor Pool That Is Conformationally Responsive to Ligand, *Journal of Biological Chemistry* 270(48), 28740-28750.
Zimmer et al. (1992) in *Peptides*, pp. 393-394, ESCOM Science Publishers.

\* cited by examiner

A

B

A

B

A

B

C

A

B

C

A

B

C

A

B

C

D

A

B

A

B

A

B

A

B

C

A

B

A

B

C

D

SEQUENCE LISTING

```
<160> NUMBER OF SEQ ID NOS: 41

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
```

```
<211> LENGTH: 25
<212> TYPE: PRT
<213> ORGANISM: Artificial Sequence
<220> FEATURE:
<223> OTHER INFORMATION: Synthetic

<400> SEQUENCE: 10

Asp Glu Leu Pro Gln Leu Val Thr Leu Pro His Pro Asn Leu His Gly
1               5                   10                  15

Pro Glu Ile Leu Asp Val Pro Ser Thr
            20                  25

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

His Gly Pro Glu Ile Leu Asp Val Pro Ser Thr
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Glu Ile Leu Asp Val
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic

<400> SEQUENCE: 13

Leu Asp Val Pro
1

<210> SEQ ID NO 14
<211> LENGTH: 4
<212> TYPE: PRT
<213> ORGANISM: Artificial Sequence
<220> FEATURE:
<223> OTHER INFORMATION: Synthetic

<400> SEQUENCE: 14

Ile Asp Ala Pro
1

<210> SEQ ID NO 15
<211> LENGTH: 8
<212> TYPE: PRT
<213> ORGANISM: Artificial Sequence
<220> FEATURE:
<223> OTHER INFORMATION: Synthetic

<400> SEQUENCE: 15

Gly Pro Glu Tyr Leu Asp Val Pro
1               5
```

```
<210> SEQ ID NO 16
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is any amino acid or any modified amino acid.

<400> SEQUENCE: 16

Xaa Cys Asp Pro Cys
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is any amino acid or any modified amino acid.
<220> FEATURE:
<221> NAME/KEY: MISC_FEATURE
<222> LOCATION: (3)..(3)
<223> OTHER INFORMATION: X is any amino acid or any modified amino acid.

<400> SEQUENCE: 17

Xaa Cys Xaa Pro Cys
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic

<400> SEQUENCE: 18

Arg Cys Asp Pro Cys
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic

<400> SEQUENCE: 19

Cys Trp Leu Asp Val Cys
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic

<400> SEQUENCE: 20

Tyr Cys Ala Pro Cys
1               5

<210> SEQ ID NO 21
```

```
<211> LENGTH: 5
<212> TYPE: PRT
<213> ORGANISM: Artificial Sequence
<220> FEATURE:
<223> OTHER INFORMATION: Synthetic

<400> SEQUENCE: 21

Tyr Cys Asp Pro Cys
1               5

<210> SEQ ID NO 22
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: d-Phe

<400> SEQUENCE: 22

Cys Asp Phe Cys
1

<210> SEQ ID NO 23
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: ThioProline

<400> SEQUENCE: 23

Arg Cys Asp Pro Cys
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: ThioProline

<400> SEQUENCE: 24

Arg Cys Asp Pro Cys
1               5

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Glu Gly Tyr Tyr Gly Asn Tyr Gly Val Tyr Ala
1               5                   10

<210> SEQ ID NO 26
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 26

Cys Tyr Tyr Gly Asn Cys
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Cys Gly Arg Gly Asp Ser Pro Cys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Arg Thr Gln Ile Asp Ser Pro Leu Asn
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Thr Gln Ile Asp Ser Pro
1               5

<210> SEQ ID NO 30
<211> LENGTH: 4
<212> TYPE: PRT
<213> ORGANISM: Artificial Sequence
<220> FEATURE:
<223> OTHER INFORMATION: Synthetic

<400> SEQUENCE: 30

Gln Ile Asp Ser
1

<210> SEQ ID NO 31
<211> LENGTH: 4
<212> TYPE: PRT
<213> ORGANISM: Artificial Sequence
<220> FEATURE:
<223> OTHER INFORMATION: Synthetic

<400> SEQUENCE: 31

Ile Asp Ser Pro
1

<210> SEQ ID NO 32
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 32

Lys Leu Glu Lys
1

<210> SEQ ID NO 33
<211> LENGTH: 8
<212> TYPE: PRT
<213> ORGANISM: Artificial Sequence
<220> FEATURE:
<223> OTHER INFORMATION: Synthetic

<400> SEQUENCE: 33

Gly Pro Glu Tyr Leu Asp Val Pro
1               5

<210> SEQ ID NO 34
<211> LENGTH: 4
<212> TYPE: PRT
<213> ORGANISM: Artificial Sequence
<220> FEATURE:
<223> OTHER INFORMATION: Synthetic

<400> SEQUENCE: 34

Leu Asp Val Pro
1

<210> SEQ ID NO 35
<211> LENGTH: 4
<212> TYPE: PRT
<213> ORGANISM: Artificial Sequence
<220> FEATURE:
<223> OTHER INFORMATION: Synthetic

<400> SEQUENCE: 35

Ile Leu Asp Val
1

<210> SEQ ID NO 36
<211> LENGTH: 21
<212> TYPE: DNA
<213> ORGANISM: Artificial Sequence
<220> FEATURE:
<223> OTHER INFORMATION: Synthetic

<400> SEQUENCE: 36
cgggatcaga aagaatccaa a                                        21

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
ctggcatggg gttaaaattg                                          20

<210> SEQ ID NO 38
<211> LENGTH: 19
<212> TYPE: DNA
<213> ORGANISM: Artificial Sequence
<220> FEATURE:
<223> OTHER INFORMATION: Synthetic
```

```
<400> SEQUENCE: 38
ccacctggtg tatgaaagc                                              19

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
ctggcatggg gttaaaattg                                             20

<210> SEQ ID NO 40
<211> LENGTH: 23
<212> TYPE: DNA
<213> ORGANISM: Artificial Sequence
<220> FEATURE:
<223> OTHER INFORMATION: Synthetic

<400> SEQUENCE: 40
gcggtctggc agtaaaaact atc                                         23

<210> SEQ ID NO 41
<211> LENGTH: 23
<212> TYPE: DNA
<213> ORGANISM: Artificial Sequence
<220> FEATURE:
<223> OTHER INFORMATION: Synthetic

<400> SEQUENCE: 41
gtgaaacagc attgctgtca ctt                                         23
```

US 8,808,698 B2

METHODS FOR INHIBITION OF LYMPHANGIOGENESIS AND TUMOR METASTASIS

The present invention claims priority to U.S. Provisional Application No. 60/765,068 filed Feb. 3, 2006.

This invention was made with government support under contract RO1CA83133-07 awarded by the National Institutes of Health (NIH). The government has certain rights in the invention.

FIELD OF THE INVENTION

The present invention is directed to compositions and methods for inhibiting the development of new lymphatic vessels, and for inhibiting tumor cell dissemination through the lymphatics. In preferred embodiments, the present invention utilizes agents that inhibit the specific binding of integrin alpha4beta1 ($\alpha 4\beta 1$, VLA-4) to one or more of its ligands. The invention further relates to methods for screening test compounds for their ability to inhibit undesirable lymphangiogenesis and/or tumor metastasis.

BACKGROUND OF THE INVENTION

Angiogenesis, the formation of new blood vessels from preexisting vessels, promotes wound healing and fertility. However, angiogenesis also promotes tumor growth and metastasis, macular degeneration and inflammatory diseases (Carmeliet et al., 2003, 2003, Nat. Med. 9:653). Lymphangiogenesis, the development of new lymphatic vessels, also occurs during tumor development (Stacker et al., 2002, Nat. Rev. Cancer 2:573; Alitalo et al., 2005, Nature 438:946). Studies have shown that tumor metastasis to the sentinel lymph nodes occurs as a result of lymphangiogenesis within tumors (Karkkainen et al., 2002, Nat. Cell Biol. 4:E2). Metastasis to other loci, such as lung and bone, may also occur as a result of lymphangiogenesis.

The molecular mechanisms that regulate the lymphatic vessels growth have been poorly understood. Recently, several specific markers of the lymphatic vessels have been described and have facilitated the lymphangiogenesis study. Two members of the VEGF family, VEGF-C and VEGF-D, have been shown to regulate lymphangiogenesis by binding the receptors VEGFR-2 and VEGFR-3 on lymphatic endothelial cells (Joukov et al., 1996, EMBO J. 15:1751; Achen et al., 2000, Eur. J. Biochem. 267:2505; Achen and Stacker, 1998, Int. J. Exp. Pathol. 79:255). In addition, the homeodomain transcription factor Prox-1 has been shown to promote lymphatic endothelium specification (Wigle et. al., 1999, Cell 98:769) and podoplanin expression (Breiteneder-Geleff et. al., 1999, Am. J. Pathol. 154:385). In addition, the CD44 family member LYVE-1 was shown to be expressed selectively by lymphatic endothelium (Banerji et al., 1999, J. Cell Biol. 144:789; and Prevo et al., 2001, J. Biol. Chem. 276:19420). LYVE1 is expressed on the cell surface as a 60-kD protein, which is reduced to approximately 40 kD by glycosidase treatment. Expression of LYVE 1, but not of CD44, largely restricted to endothelial cells lining lymphatic vessels and splenic sinusoidal endothelial cells. Expression was undetectable on lymphocytes, hematopoietic cells, or vascular endothelial cells. LYVE-1 is a useful marker to determine the localization of lymphatic endothelium by immunohistochemistry in vivo and to characterize and purify LEC in vitro.

Lymphatic vessels differ from blood vessels in several ways. Large collecting lymphatic vessels contain vascular smooth muscle cells in their wall, as well as valves, which prevent the backflow of lymph. However, lymphatic capillaries, unlike typical blood capillaries, lack pericytes and continuous basal lamina and contain large inter-endothelial valve-like openings (Casley-Smith, 1980, Lymphology 13:177; Lohela et al., 2003, Thromb. Haemost. 90:167). Due to their greater permeability, lymphatic capillaries are more effective than blood capillaries in allowing tumor cells to pass.

Many tumors express VEGF-C and VEGF-D, growth factors that selectively regulate lymphangiogenesis (Kaipainen et al., 1995, Proc. Natl. Acad. Sci. 92:3566; Saaristo et al., 2000, Oncogene 19:6122). While there are three known vascular endothelial growth factor receptors, VEGFR-1, VEGFR-2, and VEGFR-3 (Saaristo et al., 2000), only one, VEGFR-3 is expressed predominantly on lymphatic vessel. VEGF-D has been demonstrated to bind VEGFR3 and to induce endothelial cell proliferation (Achen et al., 2000; Achen and Stacker, 1998). Importantly, tumor-associated macrophages can release VEGF-C, as in human cervical cancer (Schoppman et al., 2002, Am. J. Pathol. 161:947). In fact, recent studies showed that macrophage secretion of VEGF-C and VEGF-D induces lymphangiogenesis (Cursiefen et al., 2004, J. Clin. Invest. 113:1040), thereby inducing lymphangiogenesis in tumors (Makinen et al., 2001, EMBO J. 20:4762; Stacker et al., 2002).

The integrin family of cell adhesion proteins controls cell attachment to the extracellular matrix and promotes the survival, proliferation and motility of many cell types (Kim et al., 2000, J. Biol. Chem. 275:33920; Hood and Cheresh, 2002, Nat. Rev. Cancer 2:91). Integrins transduce intracellular signals that promote cell migration and cell survival. In contrast, inhibition of integrin-ligand interaction induces apoptosis (Kim et al., 2002, J. Clin. Invest. 110:933).

At least three integrins receptors for provisional matrix proteins ($\alpha v\beta 3$, $\alpha v\beta 5$ and $\alpha 5\beta 1$) play important roles in angiogenesis (Stromblad and Cheresh, 1996, Trends Cell Biol. 6:462). The expression of integrins $\alpha 4\beta 1$, $\alpha v\beta 3$ and $\alpha 5\beta 1$ may control angiogenesis; none are expressed by quiescent endothelium but are expressed in response to angiogenic growth factors. Once they are expressed, angiogenesis depends on each integrin as antagonists of each can block angiogenesis in vivo. Recent studies show that integrin $\alpha 4\beta 1$ plays an important and unique role in angiogenesis by promoting endothelial cell-smooth muscle cell interactions during angiogenesis (Garmy-Susini et al., 2005, J. Clin. Invest. 115:1542).

Little is currently known about the roles of integrins in lymphangiogenesis, although integrin $\alpha 9\beta 1$ has been shown to be required for lymphatic development (Huang et al. 2000, Mol. Cell. Biol. 20:5208). Integrin $\alpha 9\beta 1$ has also been shown to bind directly VEGFC and VEGFD (Vlahakis et al., 2005, J. Biol. Chem. 280:4544) and to induce LEC attachment and migration. Thus there remains a need in the art for the identification of the roles of integrins in the regulation of lymphangiogenesis in cancer.

SUMMARY OF THE INVENTION

For example, in some embodiments the present invention is directed to compositions and methods for inhibiting the development of new lymphatic vessels, and for inhibiting tumor cell dissemination through the lymphatics. In preferred embodiments, the present invention utilizes agents that inhibit the specific binding of integrin alpha4beta1 ($\alpha 4\beta 1$, VLA-4) to one or more of its ligands. The invention further relates to methods for screening test compounds for their ability to inhibit undesirable lymphangiogenesis and/or tumor metastasis.

The present invention provides methods for inhibiting lymphangiogenesis in a tissue, comprising: providing: i) a tissue; and ii) an agent that interferes with specific binding of integrin alpha4beta1 to an integrin alpha4beta1 ligand; and b) contacting the tissue with the agent under conditions such that specific binding of the integrin alpha4beta1 to the integrin alpha4beta1 ligand is inhibited thereby inhibiting lymphangiogenesis in the tissue. In some embodiments, the tissue is in a subject (e.g., human or other mammal). In some preferred embodiments, the subject has a pathological condition associated with lymphangiogenesis. In particularly preferred embodiments, the tissue comprises one or more of a tumor, a tumor-proximal lymph node and a tumor-distal lymph node. In some embodiments the tumor is malignant, and in a subset of these embodiments the malignant tumor is metastatic. In some preferred embodiments, the metastatic malignant tumor is a carcinoma. In a subset of these embodiments, the carcinoma is selected from, but not limited to, a breast carcinoma and a lung carcinoma. In other preferred embodiments, the metastatic malignant tumor is a sarcoma, which in particularly preferred embodiments is a lymphangiosarcoma. In still further embodiments, the metastatic malignant tumor is a melanoma. The present invention also provides embodiments in which the agent comprises an antibody or an antigen-binding fragment of the antibody. In some preferred embodiments, the antibody is an anti-integrin alpha4beta1 antibody. In other embodiments, the antibody is selected from the group consisting of an anti-CS fibronectin antibody, and an anti-VCAM antibody. In further embodiments, the agent is selected from the group consisting of a protein (e.g., recombinant soluble VCAM), a peptide, a peptidomimetic of LDV, a peptidomimetic of RDV, a nucleic acid (e.g., antisense, siRNA, ribozyme, etc.) and a small molecule inhibitor. Also provided are embodiments in which the inhibiting lymphangiogenesis in the tissue comprises reducing the number of Lyve-1 positive vessels in the tissue. In further embodiments, the inhibiting lymphangiogenesis in the tissue further comprises reducing metastasis to a tumor-proximal lymph node or a tumor-distal lymph node.

Moreover, embodiments of the present invention provide methods for screening a test compound for inhibiting lymphangiogenesis, comprising: providing: i) a cell expressing integrin alpha4beta1; and ii) a compound to be screened; contacting the cell with the compound; and detecting inhibition of binding of the cell to an integrin alpha4beta1 ligand in the presence of the test compound, thereby identifying the test compound as inhibiting lymphangiogenesis. In some preferred embodiments, the cell expressing integrin alpha4beta 1 comprises a CD34-negative, Lyve-1-positive lymphatic endothelial cell (LEC). In a subset of these embodiments, the LEC are contacted with a growth factor before or during the contacting step. In some preferred embodiments, the growth factor comprises but is not limited to one or more of VEGF-C, VEGF-A and FGF2. The present invention also provides embodiments in which the integrin alpha4beta1 ligand comprises CS fibronectin. In other embodiments, the integrin alpha4beta1 ligand comprises VCAM. Additionally, in some embodiments the treating is in vivo, while in others, the treating is in vitro.

DEFINITIONS

Figure 1:
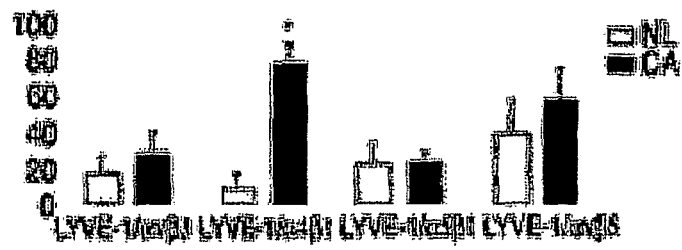
FIG. 1: Lymphatic vessel integrin expression in human tumor and normal tissues. Quantification of the percentage of integrin positive lymphatic vessels. $*p<0.001$, $**p<0.05$.× 200 magnification of cryosections.

The terms "increase," "elevate," "raise," and grammatical equivalents when used in reference to the level of a molecule (such as a protein, nucleotide sequence, etc.) or phenomenon (such as lymphangiogenesis, lymphatic metastasis, cell adhesion, cell migration, cell differentiation, angiogenesis, biological activity, biochemical activity, etc.) in a first sample relative to a second sample, mean that the quantity of the substance and/or phenomenon in the first sample is higher than in the second sample by any amount that is statistically significant using any art-accepted statistical method of analysis such as the Student's t-test. In one embodiment, the increase may be determined subjectively, for example when a patient refers to their subjective perception of disease symptoms, such as pain, clarity of vision, etc. In another embodiment, the quantity of the substance and/or phenomenon in the first sample is at least 10% greater than, preferably at least 25% greater than, more preferably at least 50% greater than, yet more preferably at least 75% greater than, and most preferably at least 90% greater than the quantity of the same substance and/or phenomenon in a second sample.

The terms "reduce," "inhibit," "diminish," "suppress," "decrease," and grammatical equivalents when used in reference to the level of a molecule (such as a protein, nucleotide sequence, etc.) or phenomenon (such as lymphangiogenesis, lymphatic metastasis, cell adhesion, cell migration, cell differentiation, angiogenesis, biological activity, biochemical activity, etc.) in a first sample relative to a second sample, mean that the quantity of substance and/or phenomenon in the first sample is lower than in the second sample by any amount that is statistically significant using any art-accepted statistical method of analysis. In one embodiment, the reduction may be determined subjectively, for example when a patient refers to their subjective perception of disease symptoms, such as pain, clarity of vision, etc. In another embodiment, the quantity of substance and/or phenomenon in the first sample is at least 10% lower than, preferably, at least 25% lower than, more preferably at least 50% lower than, yet more preferably at least 75% lower than, and most preferably at least 90% lower than the quantity of the same substance and/or phenomenon in a second sample. A reduced level of a molecule and/or phenomenon need not, although it may, mean an absolute absence of the molecule and/or phenomenon.

As used herein, the terms "inhibiting lymphangiogenesis," "diminishing lymphangiogenesis," "reducing lymphangiogenesis," and grammatical equivalents thereof refer to reducing the level of lymphangiogenesis in a tissue to a quantity which is preferably 10% less than, more preferably 50% less than, yet more preferably 75% than, even more preferably 90% less than, the quantity in a control tissue, and most preferably is at the same level which is observed in a control tissue. A reduced level of lymphangiogenesis need not, although it may, mean an absolute absence of lymphangiogenesis. The invention does not require, and is not limited to, methods that wholly eliminate lymphangiogenesis. The level of lymphangiogenesis may be determined using methods well known in the art, including, without limitation, counting the number of lymphatic vessels and/or the number of lymphatic vessel branch points, as discussed herein. An alternative means involves an in vitro cell adhesion assay that shows whether a compound inhibits the ability of (α4β1-expressing lymphatic endothelial cells (LEC) to adhere to CS-fibronectin. Other in vivo assays include the mouse metastasis assay, which shows the ability of a compound to reduce the rate of growth of transplanted tumors in certain mice, or to inhibit the formation of tumors or pre-neoplastic cells in mice which are predisposed to cancer or which express chemically-induced cancer (Humphries et al., Science, 233: 467-470, 1986 and Humphries et al., J Clin Invest, 81: 782-790, 1988).

The term "integrin α4β1" is interchangeably used with the terms "CD49d/CD29," "very late antigen 4," and "VLA4" to refer to a member of the integrin family. An "integrin" is an extracellular receptor that is expressed in a wide variety of cells and binds to specific ligands in the extracellular matrix. The specific ligands bound by integrins can contain an arginine-glycine-aspartic acid tripeptide (Arg-Gly-Asp; RGD) or a leucine-aspartic acid-valine (Leu-Asp-Val; LDV) tripeptide, and include, for example, fibronectin, vitronectin, osteopontin, tenascin, and von Willebrands's factor. Integrin α4β1 is a heterodimeric cell surface adhesion receptor composed of an α4 and β1 subunits that bind to ligands that are present in the extracellular matrix (ECM) as well as on the cell surface. An exemplary α4 polypeptide sequence is found in GenBank Accession No.XP_039012.1, and an exemplary β1 polypeptide is found in GenBank Accession No. CAA30790.1.

The term "integrin α4β1" is contemplated to include a portion of α4β1. The term "portion," when used in reference to a protein refers to a fragment of that protein. The fragments may range in size from three (3) contiguous amino acid residues to the entire amino acid sequence minus one amino acid residue. Thus, a polypeptide sequence comprising "at least a portion of an amino acid sequence" comprises from three (3) contiguous amino acid residues of the amino acid sequence to the entire amino acid sequence.

In one preferred embodiment, the portion of integrin α4β1 comprises the α4 polypeptide of sequence GenBank Accession No.XP_039012.1 or a fragment thereof. In a more preferred embodiment, the portion of the α4 polypeptide sequence comprises amino acid 141 to amino acid 301 of the sequence provided in GenBank Accession No.XP_039012.1. In a more preferred embodiment, the portion of the α4 polypeptide sequence comprises amino acid 145 to amino acid 164; amino acid 184 to amino acid 197; amino acid 219 to amino acid 224; amino acid 270 to amino acid 280; and/or amino acid 34 to amino acid 85, of the sequence shown in GenBank Accession No.XP_039012.1.

DESCRIPTION OF THE INVENTION

Certain illustrative embodiments of the invention are described below. The present invention is not limited to these embodiments.

Studies were undertaken to determine which integrins play a role in lymphangiogenesis during tumor development. In particular, the integrins α4β1, α5β1, αvβ3 and αvβ5 that have been shown to play an important role during vascular angiogenesis were evaluated.

As demonstrated herein, a single integrin, α4β1 (VLA-4) is upregulated and plays a functional role in tumor lymphangiogenesis. Integrin α4β1 mediates cell adhesion to the extracellular matrix adhesion and also cell-cell adhesion by binding to its ligands fibronectin and VCAM1, respectively. α4β1 is expressed on endothelial cells but also on leukocytes, where it plays a role in the transendothelial migration.

The expression and function of α4β1 in different models of lymphangiogenesis was determined. VEGF and bFGF have been demonstrated to synergize in the induction of angiogenesis in vitro (Pepper et al., 1992, Biochem. Biophys. Res. Commun. 189:824; Goto et al., 1993, Lab Invest. 69:508), and this observation has been confirmed in vivo in a rabbit model of hindlimb ischemia (Asahara et al., 1995, Circulation 92(Suppl. 9):II365). More recently, VEGF and bFGF have been shown to synergize with VEGF-C to induce lymphangiogenesis (Pepper et al., 1998, J. Cell Physiol. 177:439). The lymphangiogenic properties of these growth factors in a model of mouse lymphangiogenesis in MATRIGEL was also investigated. Lymphangiogenesis is induced by both of the growth factors. Expression of the integrin α4β1 on the newly formed lymphatic vessels was studied, and similar observations in a mouse model of lymphangioma were made.

To test the functionality of the integrin α4β1, human microvascular lymphatic endothelial cells were isolated and in vitro adhesion assays were performed. Results showed that only α4β1 is able to mediate attachment to the extracellular matrix (ECM). Using anti-α4β1 blocking antibodies, it was demonstrated that this integrin is crucial in the adhesion and invasion properties of lymphatic endothelial cells. In a model of VEGF-C induced lymphangiogenesis in MATRIGEL plugs, it was demonstrated that only an anti-α4β1 blocking antibody could inhibit both angiogenesis and lymphangiogenesis. These results suggest that α4β1 is the common integrin required by both blood and lymphatic growing endothelial cell to promote their adhesion to the extracellular matrix or mural cells.

Lymphangiogenesis has shown to play a role in the spread of tumors to the lymph nodes and then to secondary loci. It was demonstrated that blocking α4β1 leads to a decrease of the number of lymphatic vessels in the tumors and lymph nodes, suggesting an important role in the spreading of tumor cells via the lymphatics. To participate in the lynphangiogenic process, α4β1 must bind its ligand to induce the migration, proliferation and survival of lymphatic endothelial cells. As such, immunoreactivity of both Fibronectin and VCAM in the periphery of the lymphatic vessels in the tumors has also been demonstrated.

It is also demonstrated herein that primary tumors can precondition lymph nodes for tumor metastasis by inducing lymphangiogenesis in draining and distal lymph nodes, thereby facilitating the appearance of metastatic tumors. As such, one embodiment of the present invention provides the determination of risk of a subject for developing tumor metastasis by identifying lymphangiogenesis in lymph nodes.

The invention is further discussed below under the headings: I) Integrin α4β1 Ligands, II) Agents That Alter Binding Of Integrin α4β1 To Its Ligands, III) Other Applications and IV) Experimental and Results.

I. Integrin α4β1 Ligands

The methods of the present invention employ agents that inhibit the specific binding of integrin α4β1 with one or more of its ligands. The term "ligand" as used herein in reference to a ligand for the integrin α4β1 receptor, refers to a molecule and/or portion thereof, to which α4β1 specifically binds. In one embodiment, binding of the ligand initiates a specific biological response (e.g., lymphangiogenesis, lymphatic metastasis, angiogenesis, adhesion, migration and/or differentiation) and/or the transduction of a signal in a cell. Integrin α4β1 ligands may be present on the cell surface or present in the extracellular matrix (ECM).

In one preferred embodiment, an integrin α4β1 ligand that is present on the cell surface is exemplified by the vascular cell adhesion molecule-1 (VCAM). An example of the polypeptide sequence of VCAM is found in GenBank Accession Nos. CAA37218.1 and XP_035774.1. In another preferred embodiment, the integrin α4β1 ligand is a portion of VCAM. Preferred portions of VCAM comprise amino acid 60 to amino acid 69; amino acid 348 to amino acid 357; amino acid 103 to amino acid 106; and/or amino acid 391 to amino acid 394, of the sequences of GenBank Accession Nos. CAA37218.1 or XP 035774.1. Other portions of VCAM are also contemplated for use with the methods of the present invention.

In another preferred embodiment, an integrin α4β1 ligand that is present in the ECM is exemplified by fibronectin. An exemplary polypeptide sequence of fibronectin is found GenBank Accession No. CAA26536.1. In another preferred embodiment, the integrin α4β1 ligand is a portion of fibronectin. Preferred portions of fibronectin as exemplified in GenBank Accession No. CAA26536.1 include the IIICS sequence from amino acid 1982 to amino acid 2111, which encodes two α4β1 binding sites. In a more preferred embodiment, the portion comprises the CS-1 sequence, which contains the amino acid sequence LDV, corresponding to amino acid 2011 to amino acid 2013 of GenBank Accession No. CAA26536.1. In an alternative embodiment, the portion comprises the CS-5 sequence, which contains the amino acid sequence REDV, corresponding to amino acid 2091 to amino acid 2094 of GenBank Accession No. CAA26536.1. In another preferred embodiment, the portion comprises amino acid 1903 to amino acid 1907 of GenBank Accession No. CAA26536.1. The invention further includes portions of fibronectin that contain the afore-mentioned sequences.

In another preferred embodiment, an integrin α4β1 ligand that is present in the ECM is exemplified by fibronectin. An exemplary polypeptide sequence of fibronectin is found GenBank Accession No. CAA26536.1 (SEQ ID NO:4). In another preferred embodiment, the integrin α4β1 ligand is a portion of fibronectin. Preferred portions of fibronectin as exemplified in SEQ ID NO:4 include the IIICS sequence from amino acid 1982 to amino acid 2111, which encodes two α4β1 binding sites. In a more preferred embodiment, the portion comprises the CS-1 sequence, which contains the amino acid sequence LDV, corresponding to amino acid 2011 to amino acid 2013 of SEQ ID NO:4. In an alternative embodiment, the portion comprises the CS-5 sequence, which contains the amino acid sequence REDV, corresponding to amino acid 2091 to amino acid 2094 of SEQ ID NO:4. In another preferred embodiment, the portion comprises amino acid 1903 to amino acid 1907 of SEQ ID NO:4. The invention further includes portions of fibronectin that contain the afore-mentioned sequences.

Integrin α4β1 ligands other than VCAM, fibronectin, and portions thereof are also contemplated to be within the scope of the invention. These ligands may be determined using routine methods available to those skilled in the art. For example, the existence of antibodies against VCAM, fibronectin, and integrin α4β1 makes possible methods for isolating other integrin α4β1 ligands. One method takes advantage of an antibody characteristic known as idiotypy. Each antibody contains a unique region that is specific for an antigen. This region is called the idiotype. Antibodies themselves contain antigenic determinants; the idiotype of an antibody is an antigenic determinant unique to that molecule. By immunizing an organism with antibodies, one can raise "anti-antibodies" that recognize antibodies, including antibodies that recognize the idiotype. Antibodies that recognize the idiotype of another antibody are called anti-idiotypic antibodies. Some anti-idiotypic antibodies mimic the shape of the original antigen that the antibody recognizes and bear the "internal image" of the antigen (Kennedy, Scientific American, 255:48-56, 1986). For example, anti-idiotypic antibodies have been successfully generated against anti-ELAM1 antibodies and were found to recognize the ELAM1 ligand, which (similarly to integrin α4β1) is a molecule expressed on the surface of endothelial cells (U.S. Pat. No. 6,252,043, incorporated in its entirety by reference).

When the antigen is a ligand, certain anti-idiotypes can bind to that ligand's receptor. Several of these have been identified, including anti-idiotypes that bind to receptors for insulin, angiotensin II, adenosine I, adrenalin, and rat brain nicotine and opiate receptors (Carlsson and Glad, Bio/Technology 7:567-73, 1989).

II. Agents that Alter Binding of Integrin α4β1 to One or More of its Ligands

Some preferred methods of the present invention include the step of utilizing an agent that alters (i.e., increases or decreases) the specific binding of α4β1 to one or more of its ligands. The term "specific binding," as used herein in reference to the binding of an agent to either integrin α4β1 or an integrin α4β1 ligand, means that the interaction is dependent upon the presence of a particular structure on integrin α4β1 or its ligand, respectively. For example, if an agent is specific for epitope "A," the presence of a protein containing epitope A (or free, unlabelled A) in a reaction containing labeled "A" and the agent will reduce the amount of labeled A bound to the agent.

The terms "inhibit the specific binding" and "reduce the specific binding" when used in reference to the effect of an agent on the specific binding of integrin α4β1 with an integrin α4β1 ligand, mean that the agent reduces the level of specific binding of integrin α4β1 with its ligand to a quantity which is preferably 10% less than, more preferably 50% less than, yet more preferably 75% less than, even more preferably 90% less than, the quantity of specific binding in a control sample, and most preferably is at the same level which is observed in a control sample, as detected by (for example) an enzyme linked immunosorbant assay (ELISA). A reduced level of specific binding need not, although it may, mean an absolute absence of specific binding. The invention does not require, and is not limited to, methods that wholly eliminate specific binding of integrin α4β1 with its ligand.

The term "antagonist" is used herein to mean a molecule, (e.g., antibody) which can inhibit the specific binding of a receptor and its ligand. An anti-α4β1 integrin antibody, which inhibits the specific binding of α4β1 with fibronectin, is an example of an α4β1 antagonist. An antagonist can act as a competitive inhibitor or a noncompetitive inhibitor of α4β1 binding to its ligand.

The terms "agent," "test agent," "test compound," "compound," "molecule," and "test molecule," refer to any type of molecule (for example, a peptide, nucleic acid, carbohydrate, lipid, organic, and inorganic molecule, etc.) obtained from any source (for example, plant, animal, and environmental source, etc.), or prepared by any method (for example, purification of naturally occurring molecules, chemical synthesis, genetic engineering methods, etc.). Agents comprise both known and potential compounds. Agents are exemplified by, but not limited to, antibodies, nucleic acid sequences such as antisense and ribozyme sequences, and compounds produced by chemical libraries, phage libraries, etc. as further described below.

Without intending to limit the invention to any mechanism, and recognizing that an understanding of a mechanism is not required, it is contemplated that an agent can inhibit the specific binding of an integrin α4β1 receptor with its ligand by various mechanisms, including, for example, by binding to the binding site which is located on the ligand (e.g., VCAM) thereby inhibiting the binding of the integrin α4β1 receptor to its binding site on the ligand, or by binding to a site other than the binding site on the ligand and sterically hindering the binding of the integrin α4β1 receptor to the binding site on the ligand. Alternatively, the agent may bind to integrin α4β1 (rather than to the integrin α4β1 ligand) thereby causing a conformational or other change in the receptor that inhibits binding of integrin α4β1 to the ligand.

A. Antibodies

In one embodiment, the agent that inhibits the specific binding of α4β1 to one or more of its ligands is an antibody. The terms "antibody" and "immunoglobulin" are interchangeably used to refer to a glycoprotein or a portion thereof (including single chain antibodies), which is evoked in an animal by an immunogen and which demonstrates specificity to the immunogen, or, more specifically, to one or more epitopes contained in the immunogen. The term "antibody" expressly includes within its scope antigen binding fragments of such antibodies, including, for example, Fab, F(ab')$_2$, Fd or Fv fragments of an antibody. The antibodies of the invention also include chimeric and humanized antibodies. Antibodies may be polyclonal or monoclonal. The term "polyclonal antibody" refers to an immunoglobulin produced from more than a single clone of plasma cells; in contrast "monoclonal antibody" refers to an immunoglobulin produced from a single clone of plasma cells.

Antibodies contemplated to be within the scope of the invention include naturally occurring antibodies as well as non-naturally occurring antibodies, including, for example, single chain antibodies, chimeric, bifunctional and humanized antibodies, as well as antigen-binding fragments thereof. Naturally occurring antibodies may be generated in any species including murine, rat, rabbit, hamster, human, and simian species using methods known in the art. Non-naturally occurring antibodies can be constructed using solid phase peptide synthesis, can be produced recombinantly or can be obtained, for example, by screening combinatorial libraries consisting of variable heavy chains and variable light chains as previously described (Huse et al., Science, 246:1275-1281 1989). These and other methods of making, for example, chimeric, humanized, CDR-grafted, single chain, and bifunctional antibodies are well known to those skilled in the art (Winter and Harris, Immunol Today, 14:243-246, 1993; Ward et al., Nature, 341:544-546, 1989; Hilyard et al., Protein Engineering: A practical approach, IRL Press 1992; and Borrabeck, Antibody Engineering, 2d ed., Oxford University Press, 1995).

As used herein, the term "antibody" when used in reference to an anti-integrin antibody, particularly an anti-integrin α4β1 antibody, refers to an antibody which specifically binds to one or more epitopes on an integrin α4β1 polypeptide or peptide portion thereof, and which may or may not include some or all of an RGD binding domain. In one embodiment, an anti-integrin α4β1 antibody, or antigen binding fragment thereof, is characterized by having specific binding activity for integrin α4β1 of at least about $1 \times 10^5 M^{-1}$, more preferably at least about $1 \times 10^6 M^{-1}$, and yet more preferably at least about $1 \times 10^7 M^{-1}$.

Those skilled in the art know how to make polyclonal and monoclonal antibodies that are specific to a desirable polypeptide. For example, monoclonal antibodies may be generated by immunizing an animal (e.g., mouse, rabbit, etc.) with a desired antigen and immortalizing spleen cells obtained from the immunized animal, commonly by fusion with a myeloma cell.

Immunization with antigen may be accomplished in the presence or absence of an adjuvant (e.g., Freund's adjuvant). Typically, for a mouse, 10 μg antigen in 50-200 μl adjuvant or aqueous solution is administered per mouse by subcutaneous, intraperitoneal or intramuscular routes. Booster immunization may be given at intervals (e.g. 2-8 weeks). The final boost is given approximately 2-4 days prior to fusion and is generally given in aqueous form rather than in adjuvant.

Spleen cells from the immunized animals may be prepared by teasing the spleen through a sterile sieve into culture medium at room temperature, or by gently releasing the spleen cells into medium by pressure between the frosted ends of two sterile glass microscope slides. The cells are harvested by centrifugation (400×g for 5 min.), washed and counted.

Spleen cells are fused with myeloma cells to generate hybridoma cell lines. Several mouse myeloma cell lines which have been selected for sensitivity to hypoxanthine-aminopterin-thymidine (HAT) are commercially available and may be grown in, for example, Dulbecco's modified Eagle's medium (DMEM) (Gibco BRL) containing 10-15% fetal calf serum. Fusion of myeloma cells and spleen cells may be accomplished using polyethylene glycol (PEG) or by electrofusion using protocols that are routine in the art. Fused cells are distributed into 96-well plates followed by selection of fused cells by culture for 1-2 weeks in 0.1 ml DMEM containing 10-15% fetal calf serum and HAT. The supernatants are screened for antibody production using methods well known in the art. Hybridoma clones from wells containing cells that produce antibody are obtained (e.g., by limiting dilution). Cloned hybridoma cells ($4-5 \times 10^6$) are implanted intraperitoneally in recipient mice, preferably of a BALB/c genetic background. Sera and ascites fluids are typically collected from mice after 10-14 days.

The invention also contemplates humanized antibodies that are specific for at least a portion of integrin α4β1 and/or its ligands. Humanized antibodies may be generated using methods known in the art, including those described in U.S. Pat. Nos. 5,545,806; 5,569,825 and 5,625,126, the entire contents of which are incorporated by reference. Such methods include, for example, generation of transgenic non-human animals which contain human immunoglobulin chain genes and which are capable of expressing these genes to produce a repertoire of antibodies of various isotypes encoded by the human immunoglobulin genes.

In a preferred embodiment, the antibody is specific for (i.e., specifically binds to) integrin α4β1 and/or a portion thereof. While the invention is illustrated using antibodies to the C-terminus of fibronectin and to integrin α4β1, and using exemplary peptide antagonists to integrin α4β1 the invention is not limited to the use of these particular agents. Rather, the invention expressly includes any agent, which inhibits the specific binding of integrin α4β1 to one or more integrin α4β1 ligands. In one preferred embodiment, the anti-integrin α4β1 antibody binds integrin α4β1 with at least 2 times greater, preferably at least 5 times greater, more preferably at least 10 times greater, and yet more preferably at least 100 times greater, affinity than it binds another integrin, for example, Vβ3 and/or a Vβ5. Anti-integrin α4β1 antibodies include, without limitation, mouse anti-human integrin α4β1 antibodies such as HP2/1, HP1/3, HP 1/1, HP1/7, HP2/4 (Sanchez-Madrid et al., Eur J Immunol, 16, 1342-1349, 1986), ALC1/4.1, ALC 115.1 (Munoz et al., Biochem J, 327, 27-733, 1997), 44H6 (Quackenbush et al., J Immunol, 134: 1276-1285, 1985), P1H4, P4C2, P4G9 (Wayner et al., J Cell Biol, 109:1321, 1998), 9C10 (Kinashi et al., Blood Cells 20: 25-44, 1994), 9F10 (Hemler et al., J Biol Chem, 262: 11478, 1987), B5G10 (Hemler et al., J Biol Chem, 262, 3300-3309, 1987), 15/7 (Yednock et al., J Biol Chem, 270:28740-28750, 1995), SG/73 (Miyake et al., J Cell Biol, 119, 653-662, 1992). Also included within the scope of this invention are humanized anti-human integrin α4β1 antibodies, such as TYSABRI formerly known as ANTEGREN (natalizumab marketed by Biogen Idec) (Tubridy et al., Neurology, 53:466-72,1999; Sheremata et al., Neurology, 52:1072-1074, 1999; and Lin et al., Current Opinion in Chemical Biology, 2:453-457, 1998) and the chimeric antibodies disclosed by Newman et al., U.S. Pat. No. 5,750,105, the contents of which are incorporated by reference; rat anti-mouse integrin α4β1 antibodies such as PS/2 (Chisholm et al., Eur J Immunol, 23: 682-688, 1993); mouse anti-rat α4β1 antibodies such as TA-2 (Issekutz, J Immunol, 147:4178-4184, 1991); and rat anti-mouse α4β1 antibodies such as R1-2 (Holzmann et al., Cell, 56:37-46, 1989).

In another preferred embodiment, the antibody is specific for VCAM and/or a portion thereof. In a more preferred embodiment, the anti-VCAM antibody inhibits the binding of VCAM to α4β1 integrin but not to other integrins. Exemplary antibodies include, for example, 4B2 and 1E10, P1B8, and P3C4 (Needham et al., Cell Adhes Commun, 2:87-99, 1994; and Dittel et al., Blood, 81:2272-2282, 1993), and the chimeric antibodies disclosed by Newman et al., U.S. Pat. No. 5,750,105, the contents of which are incorporated by reference.

In yet another preferred embodiment, the antibody is specific for fibronectin and/or a portion thereof. In a more preferred embodiment, the anti-VCAM antibody inhibits the binding of VCAM to α4β1 integrin but not to other integrins. Such antibodies include, without restriction, antibodies against the major and minor integrin α4β1-binding sites in the C-terminal region of fibronectin, and antibodies against neighboring heparin-binding sites that interfere with binding of integrin α4β1 to fibronectin. Exemplary antibodies include P1F11 and P3D4 (Garcia-Pardo et al., Biochem Biophys Res Com, 186:135-42, 1992); and the antibodies 20E10, 21E5, 9E9, 16E6, 19B7, 26G10, 30B6, 36C9, and 39B6 (Mostafavi-Pour et al., Matrix Biology, 20:63-73, 2001).

B. Proteins and Peptides

In an alternative embodiment, the agent that inhibits the specific binding of integrin α4β1 to one or more of its ligands is a protein or peptide that inhibits integrin α4β1 binding to its ligand (See, e.g., WO 03/019136 A3 to Varner). The term "peptide" as used herein is used broadly to refer to at least two amino acids and/or amino acid analogs that are covalently linked by a peptide bond and/or an analog of a peptide bond. The term "protein" as used herein is used to refer to polypeptides (oligomers and polymers of amino acids and/or amino acid analogs) of more than twenty amino acids. The term peptide also includes molecules which are commonly referred to as peptides, which generally contain from about two to about twenty amino acids. The term peptide also includes molecules which are commonly referred to as polypeptides, which generally contain from about twenty to about fifty amino acids. The term peptide also includes molecules which are commonly referred to as proteins, which generally contain from about fifty to about 3000 amino acids. The amino acids of the peptide antagonists may be L-amino acids and/or D-amino acids.

The terms "derivative" or "modified" when in reference to a peptide mean that the peptide contains at least one derivative amino acid. A "derivative" of an amino acid and a "modified" amino acid are chemically modified amino acids. Derivative amino acids can be "biological" or "non-biological" amino acids. Chemical derivatives of one or more amino acid members may be achieved by reaction with a functional side group. Illustrative derivatized molecules include for example those molecules in which free amino groups have been derivatized to form amine hydrochlorides, p-toluene sulfonyl groups, carboxybenzoxy groups, t-butyloxycarbonyl groups, chloroacetyl groups and/or formyl groups. Free carboxyl groups may be derivatized to form salts, methyl and ethyl esters and/or other types of esters and hydrazides. Free hydroxyl groups may be derivatized to form O-acyl and/or O-alkyl derivatives. The imidazole nitrogen of histidine may be derivatized to form N-im-benzylhistidine. Also included as chemical derivatives are those peptides that contain naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine for lysine. Other included modifications are amino terminal acylation (e.g., acetylation or thioglycolic acid amidation), terminal carboxylamidation (e.g., with ammonia or methylamine), and similar terminal modifications. Terminal modifications are useful, as is well known, to reduce susceptibility by proteinase digestion and therefore to prolong the half-life of the peptides in solutions, particularly in biological fluids where proteases may be present. Exemplary modified amino acids include, without limitation, 2-Aminoadipic acid, 3-Aminoadipic acid, beta-Alanine, beta-Aminopropionic acid, 2-Aminobutyric acid, 4-Aminobutyric acid, piperidinic acid, 6-Aminocaproic acid, 2-Aminoheptanoic acid, 2-Aminoisobutyric acid, 3-Aminoisobutyric acid, 2-Aminopimelic acid, 2,4-Diaminobutyric acid, Desmosine, 2,2'-Diaminopimelic acid, 2,3-Diaminopropionic acid, N-Ethylglycine, N-Ethylasparagine, Hydroxylysine, allo-Hydroxylysine, 3-Hydroxyproline, 4-Hydroxyproline, Isodesmosine, allo-Isoleucine, N-Methylglycine, sarcosine, N-Methylisoleucine, N-Methylavaline, Norvaline, Norleucine, and Ornithine. Derivatives also include peptides containing one or more additions or deletions, as long as the requisite activity is maintained.

The amino acids of the peptides are contemplated to include biological amino acids as well as non-biological amino acids. The term "biological amino acid" refers to any one of the known 20 coded amino acids that a cell is capable of introducing into a polypeptide translated from an mRNA. The term "non-biological amino acid" refers to an amino acid that is not a biological amino acid. Non-biological amino acids are useful, for example, because of their stereochemistry or their chemical properties. The non-biological amino acid norleucine, for example, has a side chain similar in shape to that of methionine. However, because it lacks a side chain sulfur atom, norleucine is less susceptible to oxidation than methionine. Other examples of non-biological amino acids include aminobutyric acids, norvaline and allo-isoleucine, that contain hydrophobic side chains with different steric properties as compared to biological amino acids.

Peptides that are useful in the instant invention may be synthesized by several methods, including chemical synthesis and recombinant DNA techniques. Synthetic chemistry techniques, such as solid phase Merrifield synthesis are preferred for reasons of purity, freedom from undesired side products, ease of production, etc. A summary of the techniques available are found in several references, including Merrifield, Adv Enzymol, 32:221-96, 1969; Fields et al., Intl Peptide Protein Res, 35:161-214, 1990, and U.S. Pat. No. 4,244,946 for solid phase peptide synthesis; and Schroder et al., The Peptides, Vol 1, Academic Press, New York, 1965, for classical solution synthesis. Protecting groups usable in synthesis are known in the art. Solid phase synthesis methods consist of the sequential addition of one or more amino acid residues or suitably protected amino acid residues to a growing peptide chain. Either the amino or carboxyl group of the first amino acid residue is protected by a suitable selectively removable protecting group. A different, selectively removable protecting group is utilized for amino acids containing a reactive side group such as lysine.

The resultant linear peptides may then be reacted to form their corresponding cyclic peptides. A method for cyclizing peptides is described in Zimmer et al., Peptides, 393-394 (1992), ESCOM Science Publishers, B.V., 1993. To cyclize peptides containing two or more cysteines through the formation of disulfide bonds, the methods described by Tam et al., J Am. Chem Soc, 113:6657-6662, 1991; Plaue, Int J Peptide Protein Res, 35:510-517, 1990; Atherton, J Chem Soc Trans, 1:2065 (1985); and Kamber et al., Helv Chim Acta, 63:899 (1980) are useful. Polypeptide cyclization is a useful modification to generate modified peptides (e.g., peptidomimetics) because of the stable structures formed by cyclization and in view of the biological activities observed for cyclic peptides.

Alternatively, selected compounds of the present invention are produced by expression of recombinant DNA constructs prepared in accordance with well-known methods once the peptide sequence of interest has been identified. Such production can be desirable to provide large quantities or alternative embodiments of such compounds. Production by recombinant means may be more desirable than standard solid phase peptide synthesis for peptides of at least 8 amino acid residues. The DNA encoding the desired peptide sequence is preferably prepared using commercially available nucleic acid synthesis methods. Following these nucleic acid synthesis methods, DNA is isolated in a purified form that encodes the peptides. Methods to construct expression systems for production of peptides in recombinant hosts are also generally known in the art. Preferred recombinant expression systems, when transformed into compatible hosts, are capable of expressing the DNA encoding the peptides. Other preferred methods used to produce peptides comprise culturing the recombinant host under conditions that are effective to bring about expression of the encoding DNA to produce the peptide of the invention and ultimately to recover the peptide from the culture.

Expression can be effected in prokaryotic and eukaryotic hosts. The prokaryotes are most frequently represented by various strains of E. coli. However, other microbial strains may also be used, such as bacilli, for example Bacillus subtilis, various species of Pseudomonas, or other bacterial strains. In such prokaryotic systems, plasmid vectors that contain replication sites and control sequences derived from a species compatible with the host are used. For example, a workhorse vector for E. coli is pBR322 and its derivatives. Commonly used prokaryotic control sequences, which contain promoters for transcription initiation, optionally with an operator, along with ribosome binding-site sequences, include such commonly used promoters as the beta-lactamase (penicillinase) and lactose (lac) promoter systems, the tryptophan (trp) promoter system, and the lambda-derived $P_L$ promoter and N-gene ribosome binding site. However, any available promoter system compatible with prokaryote expression is suitable for use.

Expression systems useful in eukaryotic hosts comprise promoters derived from appropriate eukaryotic genes. A class of promoters useful in yeast, for example, includes promoters for synthesis of glycolytic enzymes (e.g., those for 3-phosphoglycerate kinase). Other yeast promoters include those from the enolase gene or the Leu2 gene obtained from YEp13. Suitable mammalian promoters include the early and late promoters from SV40 or other viral promoters such as those derived from polyoma, adenovirus II, bovine papilloma virus or avian sarcoma viruses. Suitable viral and mammalian enhancers may also be used. In the event plant cells are used as an expression system, the nopaline synthesis promoter, for example, is appropriate.

Once the expression systems are constructed using well-known restriction and ligation techniques, transformation of appropriate host cells is done using standard techniques appropriate to such cells. The cells containing the expression systems are cultured under conditions appropriate for production of the peptides, and the peptides are then recovered and purified.

In a preferred embodiment, the agent that specifically binds integrin α4β1 finds use in methods of the invention where the peptide binds to integrin α4β1 with at least about a two-fold greater, more preferably at least about five-fold greater, even more preferably at least about ten-fold greater, and most preferably at least about one hundred-fold greater, specificity for integrin α4β1 than for another integrin such as αVβ3. As such, the various RGD and RLD containing peptides that have been identified based on their relatively high binding affinity for integrin αVβ3 or for integrin αVβ5 (See, e.g., PCT/US94/13542) are not considered peptide antagonists of integrin α4β1 binding to its ligand, as defined herein.

Exemplary peptides which inhibit the specific binding of integrin α4β1 to one or more of its ligands include, without limitation, CS-1 fibronectin and fragments of CS-1 fibronectin, such as DELPQLVTLPHPNLHGPEILDVPST (SEQ ID NO:10), HGPEILDVPST (SEQ ID NO:11), and EILDV (SEQ ID NO:12) (Wayner et al., J Cell Biol, 109:1321-30, 1989); LDVP (SEQ ID NO:13) (Clements et al., J Cell Sci, 107:2127-35, 1994), LDV (Wayner et al., J Cell Biol, 116: 489-97, 1992); IDAP (SEQ ID NO:14) and RDV (Clements et al., J Cell Sci, 107:2127-35, 1994); GPEYLDVP (SEQ ID NO:15) (Bochner et al., J Exp Med, 173:1553-7, 1991); (X)C*DPC* (SEQ ID NO:16) where X is any amino acid or modified amino acid, (X) C*(X)PC* (SEQ ID NO:17) where X is any amino acid, RC*DPC* (SEQ ID NO:18), C*WLDVC* (SEQ ID NO:19), YC*APC* (SEQ ID NO:20) and YC*DPC* (SEQ ID NO:21), and phenyacyl-C*DfC* (SEQ ID NO:22) (where "f" is D-Phe) (Jackson et al., J Med Chem, 40:3359-68, 1997); RC*D(ThioP)C* (SEQ ID NO:23) (Nowlin et al., J Biol Chem, 268:20352-9, 1993); 9-fluorenecarboxylRC*D(ThioP)C* (SEQ ID NO:24) (Cardarelli et al., J Biol Chem, 269:18668-73, 1994); EGYYGNYGVYA (SEQ ID NO:25) and C*YYGNC* (SEQ ID NO:26) where * indicates cyclization points; and modifications thereof (See, e.g., Thorsett et al., WO9602644); I-adamantaneacetyl-Cys-Gly-Arg-Gly-Asp-Ser-Pro-Cys (SEQ ID NO:27) (Cardarelli et al., J Biol Chem, 269:18668-73, 1994). Other exemplary peptides include snake disintegrins, which are exemplified by, but not limited to, EC3 from Echis carinatus, EC3B, which is a subunit of EC3, a peptide fragment of EC3; and modifications thereof (Brando et al., Biochem Biophys Res Commun, 267:413-417, 1000; and Marcinkiewicz et al., J Biol Chem 274:1 2468-73, 1999); soluble VCAM (Rose et al., Blood, 95:602-609, 2000); soluble VCAM fragments (Dudgeon et al., Eur J Biochem, 226:517-23, 1994); VCAM peptide sequences RTQIDSPLN (SEQ ID NO:28), TQIDSP (SEQ ID NO:29), QIDS (SEQ ID NO:30), IDSP (SEQ ID NO:31) and KLEK (SEQ ID NO:32) (Clements et al., J Cell Sci, 107:2127-35, 1994).

Figure 15:
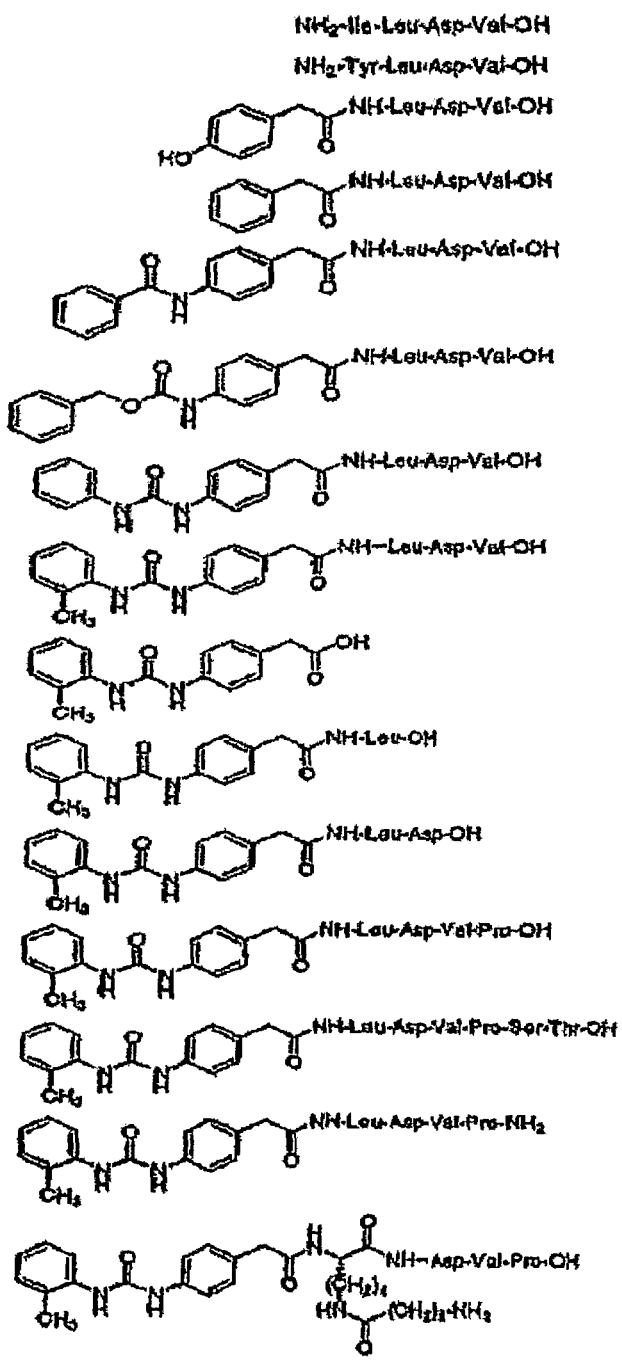
FIG. 15 shows exemplary agents that inhibit binding of integrin α4β1 to VCAM.
Figure 16:
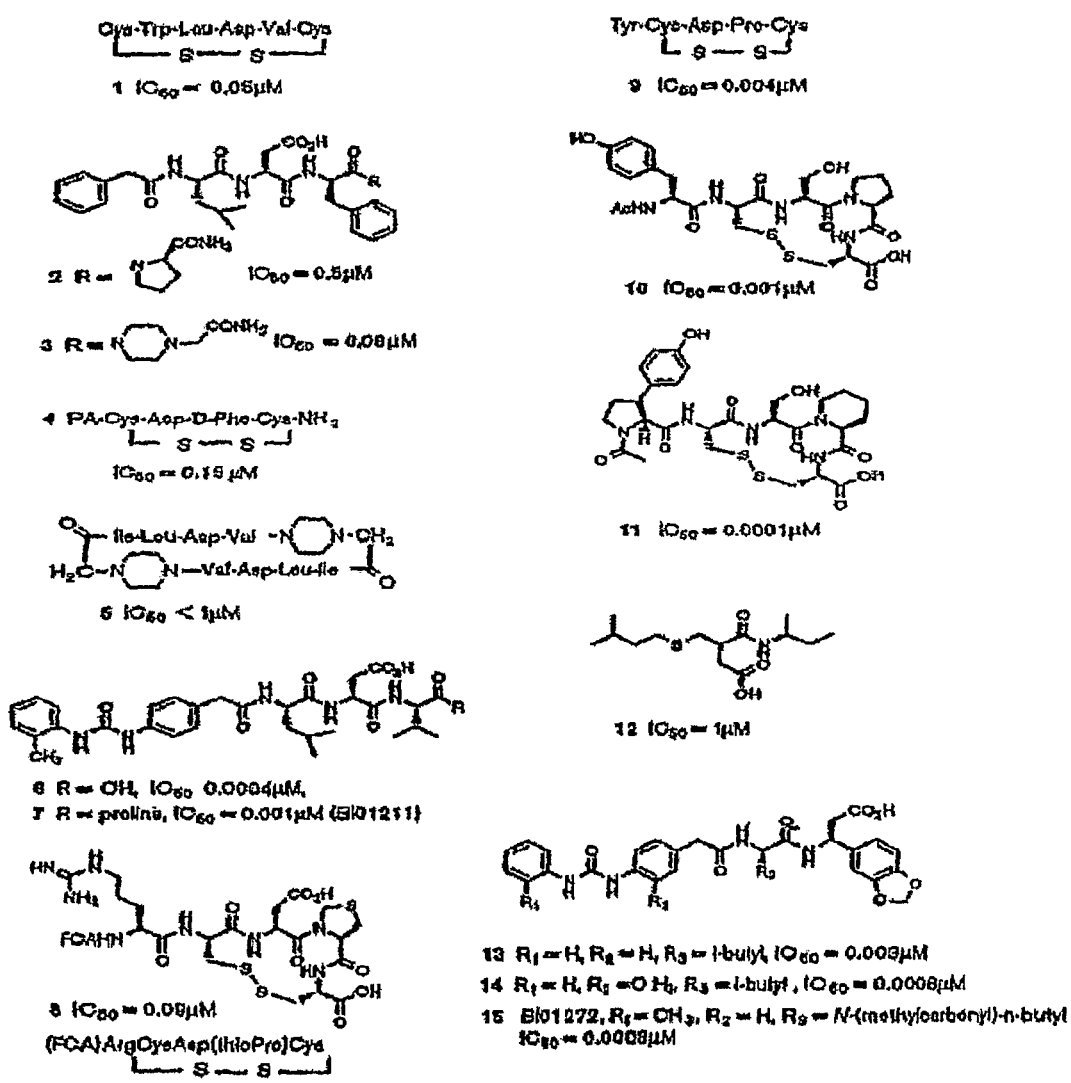
FIG. 16 shows exemplary agents that inhibit binding of integrin α4β1 to its ligands, with IC50 values based on direct binding assays. In this figure, the abbreviations are as follows: FCA, 9-fluorenecarboxyl; IC, inhibition concentration; PA, phenylacetyl.
Figure 17:
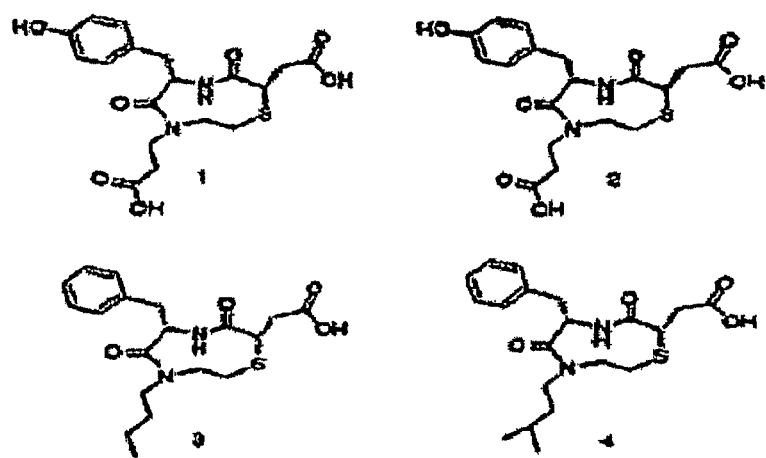
FIG. 17 shows exemplary β-turn mimetics that inhibit binding of integrin α4β1 to fibronectin.

Further exemplary modified peptides that inhibit the specific binding of integrin α4β1 to one or more of its ligands include a peptidomimetic (i.e., an organic molecules that mimics the structure of a peptide); or a peptoid such as a vinylogous peptoid. Examples of cyclic peptides and peptidomimetics which are within the scope of the invention include, without limitation, those which are based on the peptide structure GPEYLDVP (SEQ ID NO:33), such as the compound named TBC722 (Kogan et al., WO9600581), based on the peptide structure LDVP (SEQ ID NO:34) including phenylacetyl LDFp (Arrhenius et al., WO9515973; and Arrhenius et al., WO9606108), based on the peptide structure ILDV (SEQ ID NO:35) (Dutta, WO9702289), BIO1211 (4-(2-methylphenylluriedo)phenylacetyl LDVP) BIO1272 (Lin et al., WO9200995; Lin et al., WO9622966), CY9652 a CS-1 peptidomimetic, TBC3342, ZD-7349 (Curley et al. (1999) Cell. Mol. Life Sci., 56:427-441); and others (EP-842943-A2, WO9842656-A1, WO9620216-A1, WO9600581-A1, Souers et al., Bioorg Med Chem Lett, 8:2297-2302, 1998). Exemplary peptides and modified peptides are illustrated in FIG. 15 (See, Lin et al., J Med Chem, 42:920-934, 1999), FIG. 16 (See, Lin et al., Curr Opin Chem Biol, 2:453-457, 1998), and FIG. 17 (See, Souers et al., Bioorg. Med Chem Lett, 8:2297-2302, 1998). Methods for generating libraries of mimetics and for evaluating the library of mimetics for inhibiting the binding of receptors to their ligands are known in the art (Souers et al., supra, 1998).

Other peptides useful as α4β1 antagonists that reduce angiogenesis can be purchased from commercial sources, and can be identified by screening libraries of peptides, which can be prepared using known methods of chemical synthesis (Koivunen et al., J Cell Biol, 124:373-380, 1994). For example, peptide agonists of integrin α4β1 other than those specifically disclosed herein may be identified using methods known in the art, such as by panning phage-display peptide libraries as described in U.S. Pat. No. 5,780,426 to Palladino et al., the entire contents of which are herein incorporated by reference. For example, phage-display peptide libraries are panned with the integrin α4β1 receptor attached to a solid support, such as small diameter (1 μm) polystyrene latex beads. Phage selected by this method can then be tested for specific binding to integrin α4β1 via ELISA or other immunologically-based assays. Individual peptide sequences are then determined via sequencing of phage DNA. Further analysis of the minimal peptide sequence required for binding can be assessed via deletion and site-directed mutagenesis, followed by testing of the phage for binding to integrin α4β1 via ELISA. Since the identified peptide candidates are fused to the major phage coat protein, soluble peptides are then chemically synthesized and the activity of these free peptides are tested in various in vitro and in vivo assays for the ability to act as antagonists of the integrin α4β1 receptor.

C. Nucleic Acids

In an alternative embodiment, the agent that inhibits the specific binding of α4β1 to one or more of its ligands is a nucleic acid. The terms "nucleic acid" and "polynucleotide" as used herein refer to two or more nucleotides that are covalently linked to each other. Included within this definition are oligonucleotides, polynucleotides, and fragments and/or portions thereof, DNA and/or RNA of genomic and/or synthetic origin, which may be single- or double-stranded, and represent the sense or antisense strand. Nucleic acid sequences that are particularly useful in the instant invention include, without limitation, antisense sequences and ribozymes. The nucleic acid sequences are contemplated to bind to genomic DNA sequences or RNA sequences that encode integrin α4β1 or one or more of its ligands, thereby inhibiting the binding of integrin α4β1 with one or more of its ligands. Antisense and ribozyme sequences may be delivered to cells by transfecting the cell with a vector that expresses the antisense nucleic acid or the ribozyme as an mRNA molecule. Alternatively, delivery may be accomplished by entrapping ribozymes and antisense sequences in liposomes.

1. Antisense Sequences

Antisense sequences have been successfully used to inhibit the expression of several genes (Markus-Sekura, Anal Biochem, 172:289-295, 1988; Hambor et al., J Exp Med, 168: 1237-1245, 1988; and EP 140 308), including the gene encoding VCAM1, one of the integrin α4β1 ligands (U.S. Pat. No. 6,252,043, incorporated in its entirety by reference). The terms "antisense DNA sequence" and "antisense sequence" as used herein interchangeably refer to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Sense mRNA generally is ultimately translated into a polypeptide. Thus, an "antisense DNA sequence" is a sequence which has the same sequence as the non-coding strand in a DNA duplex, and which encodes an "antisense RNA" (i.e., a ribonucleotide sequence whose sequence is complementary to a "sense mRNA" sequence). The designation (−) (i.e., "negative") is sometimes used in reference to the antisense strand, with the designation (+) sometimes used in reference to the sense (i.e., "positive") strand. Antisense RNA may be produced by any method, including synthesis by splicing an antisense DNA sequence to a promoter that permits the synthesis of antisense RNA. The transcribed antisense RNA strand combines with natural mRNA produced by the cell to form duplexes. These duplexes then block either the further transcription of the mRNA or its translation, or promote its degradation.

Any antisense sequence is contemplated to be within the scope of this invention if it is capable of reducing the level of expression of integrin α4β1 and/or one or more of its ligands (e.g., VCAM and fibronectin) to a quantity which is less than the quantity of integrin α4β1 or integrin α4β1 ligand expression in a control tissue which is (a) not treated with the antisense integrin α4β1 or integrin α4β1 ligand sequence, (b) treated with a sense integrin α4β1 or integrin α4β1 ligand sequence, or (c) treated with a nonsense sequence.

The terms "reducing the level of expression of integrin α4β1 or integrin α4β1 ligand," "diminishing integrin α4β1 or integrin α4β1 ligand expression" and grammatical equivalents thereof, refer to reducing the level of integrin α4β1 or integrin α4β1 ligand expression to a quantity which is preferably 20% less than the quantity in a control tissue, more preferably is 50% less than the quantity in a control tissue, yet more preferably is 90% less than the quantity in a control tissue, and most preferably is at the background level of, or is undetectable by, a Western blot analysis of integrin α4β1 or integrin α4β1 ligand, by immunofluorescence for detection of integrin α4β1 or integrin α4β1 ligand, by reverse transcription polymerase chain (RT-PCR) reaction for detection of integrin α4β1 or integrin α4β1 ligand mRNA, or by in situ hybridization for detection of integrin α4β1 or integrin α4β1 ligand MRNA. When a background level or undetectable level of integrin α4β1 or integrin α4β1 ligand peptide or MRNA is measured, this may indicate that integrin α4β1 or integrin α4β1 ligand is not expressed. A reduced level of integrin α4β1 or integrin α4β1 ligand need not, although it may, mean an absolute absence of expression of integrin α4β1 or integrin α4β1 ligand. The invention does not require, and is not limited to, antisense integrin α4β1 or integrin α4β1 ligand sequences that eliminate expression of integrin α4β1 or integrin α4β1 ligand.

Antisense integrin α4β1 or integrin α4β1 ligand sequences capable of reducing the level of integrin α4β1 expression include, for example, sequences which are capable of hybridizing with at least a portion of integrin α4β1 cDNA or integrin α4β1 ligand cDNA under high stringency or medium stringency conditions. Antisense integrin α4β1 sequences and antisense integrin α4β1 ligand sequences within the scope of this invention may be designed using approaches known in the art. In a preferred embodiment, the antisense integrin α4β1 sequences and antisense integrin α4β1 ligand sequences are designed to be hybridizable to integrin α4β1 mRNA or to integrin α4β1 ligand mRNA which is encoded by the coding region of the integrin α4β1 gene and the integrin α4β1 ligand gene, respectively. Alternatively, antisense integrin α4β1 or integrin α4β1 ligand sequences may be designed to reduce transcription by hybridizing to upstream-nontranslated sequences, thereby preventing promoter binding to transcription factors.

In a preferred embodiment, the antisense oligonucleotide sequences of the invention range in size from about 8 to about 100 nucleotide residues. In yet a more preferred embodiment, the oligonucleotide sequences range in size from about 8 to about 30 nucleotide residues. In a most preferred embodiment, the antisense sequences have 20 nucleotide residues.

However, the invention is not intended to be limited to the number of nucleotide residues in the oligonucleotide sequence disclosed herein. Any oligonucleotide sequence that is capable of reducing expression of integrin α4β1 or of integrin α4β1 ligand is contemplated to be within the scope of this invention. For example, oligonucleotide sequences may range in size from about 3 nucleotide residues to the entire integrin α4β1 or integrin α4β1 ligand cDNA sequence. The art skilled know that the degree of sequence uniqueness decreases with decreasing length, thereby reducing the specificity of the oligonucleotide for the integrin α4β1 mRNA, or integrin α4β1 ligand mRNA.

The antisense oligonucleotide sequences that are useful in the methods of the instant invention comprises naturally occurring nucleotide residues as well as nucleotide analogs. Nucleotide analogs include, for example, nucleotide residues that contain altered sugar moieties, altered inter-sugar linkages (e.g., substitution of the phosphodiester bonds of the oligonucleotide with sulfur-containing bonds, phosphorothioate bonds, alkyl phosphorothioate bonds, N-alkyl phosphoramidates, phosphorodithioates, alkyl phosphonates and short chain alkyl or cycloalkyl structures), or altered base units. Oligonucleotide analogs are desirable, for example, to increase the stability of the antisense oligonucleotide compositions under biologic conditions since natural phosphodiester bonds are not resistant to nuclease hydrolysis. Oligonucleotide analogs may also be desirable to improve incorporation efficiency of the oligonucleotides into liposomes, to enhance the ability of the compositions to penetrate into the cells where the nucleic acid sequence whose activity is to be modulated is located, in order to reduce the amount of antisense oligonucleotide needed for a therapeutic effect thereby also reducing the cost and possible side effects of treatment.

Antisense oligonucleotide sequences are synthesized using any of a number of methods known in the art, as well as using commercially available services (e.g., Genta, Inc.). Synthesis of antisense oligonucleotides may be performed, for example, using a solid support and commercially available DNA synthesizers. Alternatively, antisense oligonucleotides may also be synthesized using standard phosphoramidate chemistry techniques. For example, it is known in the art that for the generation of phosphodiester linkages, the oxidation is mediated via iodine, while for the synthesis of phosphorothioates, the oxidation is mediated with 3H-1,2-benzodithiole-3-one,1,-dioxide in acetonitrile for the step-wise thioation of the phosphite linkages. The thioation step is followed by a capping step, cleavage from the solid support, and purification on HPLC, e.g., on a PRP-1 column and gradient of acetonitrile in triethylammonium acetate, pH 7.0.

In one embodiment, the antisense DNA sequence is an "integrin α4β1 antisense DNA sequence" (i.e., an antisense DNA sequence which is designed to bind with at least a portion of the integrin α4β1 genomic sequence or with integrin α4β1 mRNA). The design of integrin α4β1 antisense DNA sequences is facilitated by the availability of the sequences for the integrin α4 subunit cDNA (GENBANK Accession No. XM_039012), and integrin β1 cDNA (GENBANK Accession No. X07979). Particularly preferred antisense sequences are those that hybridize with genomic DNA or with RNA encoding a portion of integrin α4β1 involved in the specific binding with one or more of its ligands.

In another embodiment, the antisense DNA sequence is a "vascular cell adhesion molecule antisense DNA sequence," i.e., and antisense DNA sequence which is designed to bind with at least a portion of the VCAM genomic sequence or with VCAM mRNA. The selection and design of these antisense sequences is made possible by the availability of VCAM cDNA sequences (GENBANK Accession No. X53051). Exemplary preferred antisense sequences are those that hybridize with genomic DNA or with RNA encoding a portion of VCAM involved in the specific binding of VCAM with integrin α4β1.

In yet another embodiment, the antisense DNA sequence is a "fibronectin antisense DNA sequence" (i.e., an antisense DNA sequence which is designed to bind with at least a portion of the fibronectin genomic sequence or with fibronectin mRNA). The selection and design of these antisense sequences is made possible by the availability of the sequence for fibronectin cDNA (GENBANK Accession No. X02761).

In another embodiment, the antisense DNA sequence is a "vascular cell adhesion molecule antisense DNA sequence," i.e., and antisense DNA sequence which is designed to bind with at least a portion of the VCAM genomic sequence or with VCAM mRNA. The selection and design of these antisense sequences is made possible by the availability of VCAM cDNA sequences (GENBANK Accession No. X53051; SEQ ID NO:7). Exemplary preferred antisense sequences are those that hybridize with genomic DNA or with RNA encoding a portion of VCAM involved in the specific binding of VCAM with integrin α4β1.

In yet another embodiment, the antisense DNA sequence is a "fibronectin antisense DNA sequence" (i.e., an antisense DNA sequence which is designed to bind with at least a portion of the fibronectin genomic sequence or with fibronectin mRNA). The selection and design of these antisense sequences is made possible by the availability of the sequence for fibronectin cDNA (GENBANK Accession No. X02761; SEQ ID NO:8).

2. Ribozyme

In some alternative embodiments, the agent that inhibits the specific binding of integrin α4β1 to its ligand is a ribozyme. Ribozyme sequences have been successfully used to inhibit the expression of several genes including the gene encoding VCAM1, which is one of the integrin α4β1 ligands (U.S. Pat. No. 6,252,043, incorporated in its entirety by reference).

The term "ribozyme" refers to an RNA sequence that hybridizes to a complementary sequence in a substrate RNA and cleaves the substrate RNA in a sequence specific manner at a substrate cleavage site. Typically, a ribozyme contains a "catalytic region" flanked by two "binding regions." The ribozyme binding regions hybridize to the substrate RNA, while the catalytic region cleaves the substrate RNA at a "substrate cleavage site" to yield a "cleaved RNA product." The nucleotide sequence of the ribozyme binding regions may be completely complementary or partially complementary to the substrate RNA sequence with which the ribozyme binding regions hybridize. Complete complementarity is preferred, in order to increase the specificity, as well as the turnover rate (i.e., the rate of release of the ribozyme from the cleaved RNA product), of the ribozyme. Partial complementarity, while less preferred, may be used to design a ribozyme-binding region containing more than about 10 nucleotides. While contemplated to be within the scope of the claimed invention, partial complementarity is generally less preferred than complete complementarity since a binding region having partial complementarity to a substrate RNA exhibits reduced specificity and turnover rate of the ribozyme when compared to the specificity and turnover rate of a ribozyme which contains a binding region having complete complementarity to the substrate RNA. A ribozyme may hybridize to a partially or completely complementary DNA sequence but cannot cleave the hybridized DNA sequence since ribozyme cleavage requires a 2'-OH on the target molecule, which is not available on DNA sequences.

The ability of a ribozyme to cleave at a substrate cleavage site may readily be determined using methods known in the art. These methods include, but are not limited to, the detection (e.g., by Northern blot analysis as described herein, reverse-transcription polymerase chain reaction (RT-PCR), in situ hybridization and the like) of reduced in vitro or in vivo levels of RNA which contains a ribozyme substrate cleavage site for which the ribozyme is specific, compared to the level of RNA in controls (e.g., in the absence of ribozyme, or in the presence of a ribozyme sequence which contains a mutation in one or both unpaired nucleotide sequences which renders the ribozyme incapable of cleaving a substrate RNA).

Ribozymes contemplated to be within the scope of this invention include, but are not restricted to, hammerhead ribozymes (See e.g., Reddy et al., U.S. Pat. No. 5,246,921; Taira et al., U.S. Pat. No. 5,500,357, Goldberg et al., U.S. Pat. No. 5,225,347, the contents of each of which are herein incorporated by reference), Group I intron ribozyme (Kruger et al., Cell, 31:147-157, 1982), ribonuclease P (Guerrier-Takada et al., Cell 35: 849-857, 1983), hairpin ribozyme (Hampel et al., U.S. Pat. No. 5,527,895 incorporated by reference), and hepatitis delta virus ribozyme (Wu et al., Science 243:652-655, 1989).

A ribozyme may be designed to cleave at a substrate cleavage site in any substrate RNA so long as the substrate RNA contains one or more substrate cleavage sequences, and the sequences flanking the substrate cleavage site are known. In effect, expression in vivo of such ribozymes and the resulting cleavage of RNA transcripts of a gene of interest reduces or ablates expression of the corresponding gene.

For example, where the ribozyme is a hammerhead ribozyme, the basic principle of a hammerhead ribozyme design involves selection of a region in the substrate RNA which contains a substrate cleavage sequence, creation of two stretches of antisense oligonucleotides (i.e., the binding regions) which hybridize to sequences flanking the substrate cleavage sequence, and placing a sequence which forms a hammerhead catalytic region between the two binding regions.

In order to select a region in the substrate RNA containing candidate substrate cleavage sites, the sequence of the substrate RNA needs to be determined. The sequence of RNA encoded by a genomic sequence of interest is readily determined using methods known in the art. For example, the sequence of an RNA transcript may be arrived at either manually, or using available computer programs (e.g., GENEWORKS, from IntelliGenetic Inc., or RNADRAW available from the internet), by changing the T in the DNA sequence encoding the RNA transcript to a U.

Substrate cleavage sequences in the target RNA may be located by searching the RNA sequence using available computer programs. For example, where the ribozyme is a hammerhead ribozyme, it is known in the art that the catalytic region of the hammerhead ribozyme cleaves only at a substrate cleavage site which contains a NUH, where N is any nucleotide, U is a uridine, and H is a cytosine (C), uridine (U), or adenine (A) but not a guanine (G). The U-H doublet in the NUH cleavage site does not include a U-G doublet since a G would pair with the adjacent C in the ribozyme and prevent ribozyme cleavage. Typically, N is a G and H is a C. Consequently, GUC has been found to be the most efficient substrate cleavage site for hammerhead ribozymes, although ribozyme cleavage at CUC is also efficient.

In a preferred embodiment, the substrate cleavage sequence is located in a loop structure or in an unpaired region of the substrate RNA. Computer programs for the prediction of RNA secondary structure formation are known in the art and include, for example, "RNADRAW", "RNAFOLD" (Hofacker et al., Monatshefte F. Chemie, 125:167-188, 1994; and McCaskill Biopolymers 29:1105-1119, 1990). "DNASIS" (Hitachi), and "THE VIENNA PACKAGE."

In addition to the desirability of selecting substrate cleavage sequences which are located in a loop structure or an unpaired region of the substrate RNA, it is also desirable, though not required, that the substrate cleavage sequence be located downstream (i.e., at the 3'-end) of the translation start codon (AUG or GUG) such that the translated truncated polypeptide is not biologically functional.

In a preferred embodiment, the ribozyme is an "integrin α4β1 ribozyme" (i.e., a ribozyme whose substrate cleavage sequence is designed to hybridize with a portion of integrin α4β1 that is involved in the specific binding of integrin α4β1 with one or more of its ligands). In an alternative embodiment, the substrate cleavage sequence is designed to hybridize with a portion of an integrin α4β1 ligand, wherein the portion is involved in the specific binding of the ligand with integrin α4β1.

In a more preferred embodiment, the ribozyme is a "vascular cell adhesion molecule ribozyme" (i.e., a ribozyme whose substrate cleavage sequence is designed to hybridize with a portion of VCAM that is involved in the specific binding of VCAM with integrin α4β1).

In an alternative preferred embodiment, the ribozyme is a "fibronectin ribozyme" (i.e., a ribozyme whose substrate cleavage sequence is designed to hybridize with a portion of fibronectin that is involved in the specific binding of fibronectin with integrin α4β1).

It is known in the art that the specificity of ribozyme cleavage for a substrate RNA molecule is determined by the sequence of nucleotides which flank the substrate cleavage site and which hybridize with the ribozyme binding regions. Thus, ribozymes can be designed to cleave at different locations within a substrate RNA molecule by altering the sequence of the binding regions that surround the ribozyme catalytic region of the ribozyme such that the binding regions hybridize with any known sequence on the substrate RNA.

In addition to varying the sequence of the binding regions to effect binding to different locations on the RNA substrate, the number of nucleotides in each of the ribozyme binding regions may also be altered in order to change the specificity of the ribozyme for a given location on the RNA substrate. The number of nucleotides in a binding region is preferably between about 5 and about 25 nucleotides, more preferably between about 11 and about 15 nucleotides, yet more preferably between about 7 nucleotides and about 10 nucleotides.

One of skill in the art appreciates that it is not necessary that the two binding regions that flank the ribozyme catalytic region be of equal length. Binding regions that contain any number of nucleotides are contemplated to be within the scope of this invention so long as the desirable specificity of the ribozyme for the RNA substrate and the desirable cleavage rate of the RNA substrate are achieved. One of skill in the art knows that binding regions of longer nucleotide sequence, while increasing the specificity for a particular substrate RNA sequence, may reduce the ability of the ribozyme to dissociate from the substrate RNA following cleavage to bind with another substrate RNA molecule, thus reducing the rate of cleavage. On the other hand, though binding regions with shorter nucleotide sequences may have a higher rate of dissociation and cleavage, specificity for a substrate cleavage site may be compromised.

It is well within the skill of the art to determine an optimal length for the binding regions of a ribozyme such that a desirable specificity and rate of cleavage are achieved. Both the specificity of a ribozyme for a substrate RNA and the rate of cleavage of a substrate RNA by a ribozyme may be determined by, for example, kinetic studies in combination with Northern blot analysis or nuclease protection assays.

In a preferred embodiment, the complementarity between the ribozyme binding regions and the substrate RNA is complete. However, the invention is not limited to ribozyme sequences in which the binding regions show complete complementarity with the substrate RNA. Complementarity may be partial, so long as the desired specificity of the ribozyme for a substrate cleavage site and the rate of cleavage of the substrate RNA are achieved. Thus, base changes may be made in one or both of the ribozyme binding regions as long as substantial base pairing with the substrate RNA in the regions flanking the substrate cleavage sequence is maintained and base pairing with the substrate cleavage sequence is minimized. The term "substantial base pairing" means that greater than about 65%, more preferably greater than about 75%, and yet more preferably greater than about 90% of the bases of the hybridized sequences are base-paired.

It may be desirable to increase the intracellular stability of ribozymes expressed by an expression vector. This is achieved by designing the expressed ribozyme such that it contains a secondary structure (e.g., stem-loop structures) within the ribozyme molecule. Secondary structures suitable for stabilizing ribozymes include, but are not limited to, stem-loop structures formed by intra-strand base pairs. An alternative to the use of a stem-loop structure to protect ribozymes against ribonuclease degradation is by the insertion of a stem loop at each end of the ribozyme sequence (Sioud and Drlica, Proc Natl Acad Sci, USA 88:7303-7307, 1991). Other secondary structures which are useful in reducing the susceptibility of a ribozyme to ribonuclease degradation include hairpin, bulge loop, interior loop, multibranched loop, and pseudoknot structure as described in "Molecular and Cellular Biology," Stephen L. Wolfe (Ed.), Wadsworth Publishing Company, p. 575, 1993. Additionally, circularization of the ribozyme molecule protects against ribonuclease degradation since exonuclease degradation is initiated at either the 5'-end or 3'-end of the RNA. Methods of expressing a circularized RNA are known in the art (see, e.g., Puttaraju et al., Nucl Acids Res, 21:4253-4258, 1993).

Once a ribozyme with desirable binding regions, a catalytic region and nuclease stability has been designed, the ribozyme may be produced by any known means including chemical synthesis. Chemically synthesized ribozymes may be introduced into a cell by, for example, microinjection electroporation, lipofection, etc. In a preferred embodiment, ribozymes are produced by expression from an expression vector that contains a gene encoding the designed ribozyme sequence.

3. RNAi

RNAi refers to the introduction of homologous double stranded RNA (dsRNA) to target a specific gene product, resulting in post transcriptional silencing of that gene. This phenomena was first reported in *Caenorhabditis elegans* by Guo and Kemphues (Par-1, A gene required for establishing polarity in *C. elegans* embryos, encodes a putative Ser/Thr kinase that is asymmetrically distributed, 1995, Cell, 81 (4) 611-620) and subsequently Fire et al., 1998, Nature 391: 806-811 discovered that it is the presence of dsRNA, formed from the annealing of sense and antisense strands present in the in vitro RNA preps, that is responsible for producing the interfering activity.

In some embodiments, the present invention contemplates the use of RNA interference (RNAi) to inhibit the specific binding of integrin $\alpha 4\beta 1$ to one or more of its ligands. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs.

Carthew has reported (Curr. Opin. Cell Biol. 13(2):244-248 (2001) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

In preferred embodiments, the dsRNA used to initiate RNAi, may be isolated from native sources or produced by known means, e.g., transcribed from DNA. RNA is synthesized either in vivo or in vitro. In some embodiments, endogenous RNA polymerase of the cell may mediate transcription in vivo, or cloned RNA polymerase can be used for transcription in vivo or in vitro. In other embodiments, the RNA is provided by transcription from a transgene in vivo or an expression construct. In some embodiments, the RNA strands are polyadenylated; in other embodiments, the RNA strands are capable of being translated into a polypeptide by a cell's translational apparatus. In still other embodiments, the RNA is chemically or enzymatically synthesized by manual or automated reactions. In further embodiments, the RNA is synthesized by a cellular RNA polymerase or a bacteriophage RNA polymerase (e.g., T3, T7, SP6). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. In some embodiments, the RNA is dried for storage or dissolved in an aqueous solution. In other embodiments, the solution contains buffers or salts to promote annealing, and/or stabilization of the duplex strands.

In some embodiments, the dsRNA is transcribed from the vectors as two separate stands. In other embodiments, the two strands of DNA used to form the dsRNA may belong to the same or two different duplexes in which they each form with a DNA strand of at least partially complementary sequence. When the dsRNA is thus produced, the DNA sequence to be transcribed is flanked by two promoters, one controlling the transcription of one of the strands, and the other that of the complementary strand. These two promoters may be identical or different. In some embodiments, a DNA duplex provided at each end with a promoter sequence can directly generate RNAs of defined length, and which can join in pairs to form a dsRNA. See, e.g., U.S. Pat. No. 5,795,715, incorporated herein by reference. RNA duplex formation may be initiated either inside or outside the cell.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript. The length of the identical nucleotide sequences may be at least 25, 50, 100, 200, 300 or 400 bases.

There is no upper limit on the length of the dsRNA that can be used. For example, the dsRNA can range from about 21 base pairs (bp) of the gene to the full length of the gene or more. In one embodiment, the dsRNA used in the methods of the present invention is about 1000 bp in length. In another embodiment, the dsRNA is about 500 bp in length. In yet another embodiment, the dsRNA is about 22 bp in length.

In some preferred embodiments, the sequences that mediate RNAi are from about 21 to about 23 nucleotides. That is, the isolated RNAs of the present invention mediate degradation of the target RNA (e.g., integrin α4β1). For example, siRNA or dsRNA constructs target portions of SEQ ID NOS: 5, 6, 7, or 8, thereby allowing for post-transcritional silencing of those integrin subunits as described herein, thereby inhibiting integrin α4β1 from binding to its ligand(s).

The double stranded RNA of the present invention need only be sufficiently similar to natural RNA that it has the ability to mediate RNAi for the target RNA. In one embodiment, the present invention relates to RNA molecules of varying lengths that direct cleavage of specific mRNA to which their sequence corresponds. It is not necessary that there be perfect correspondence of the sequences, but the correspondence must be sufficient to enable the RNA to direct RNAi cleavage of the target MRNA. In a particular embodiment, the RNA molecules of the present invention comprise a 3' hydroxyl group. In some embodiments, the amount of target RNA (MRNA) is reduced in the cells of the target organism (e.g., humans, non-humans) exposed to target specific double stranded RNA as compared to target organisms that have not been exposed to target specific double stranded RNA.

In one embodiment, the present invention utilizes RNAi genes encoding dsRNA sequences that target integrin α4β1 genes. In some embodiments, the integrin α4β1 genes targeted are found in humans and non-human animals.

In some embodiments, the present invention provides transgenic animals that express dsRNA molecules that correspond to target integrin α4β1 genes.

D. Other Agents

While the present invention is illustrated herein using antibody, peptide, and nucleic acid sequences that inhibit the specific binding of integrin α4β1 to one or more of its ligands, the invention expressly contemplates within its scope other agents (e.g., organic molecules, inorganic molecules, etc.) so long as the agent is capable of inhibiting the specific binding of integrin α4β1 to one or more of its ligands. Such agents are identified by screening libraries of test compounds in a competitive binding or cell adhesion assay. In a competitive binding assay, for example, integrin α4β1 is coated on plastic microtiter plates and contacted with a labeled known integrin α4β1 ligand (e.g., CS-1 fibronectin or VCAM). The test compounds are tested for their ability to inhibit binding of the labeled ligand to integrin α4β1. Compounds that inhibit such binding are identified as agents that are capable of inhibiting the specific binding of integrin α4β1 to the ligand.

Alternatively, in a cell adhesion assay, a labeled known integrin α4β1 ligand (e.g., CS-1 fibronectin or VCAM) is coated on culture plates, and cells which express integrin α4β1 are allowed to adhere to the ligand for 20-30 minutes in the presence of libraries of test compounds. Compounds that inhibit the binding of the integrin α4β1-expressing cells to the coating of integrin α4β1 ligand are identified as agents that inhibit the specific binding of integrin α4β1 to the ligand.

III. Other Applications

The present invention further provides for compositions and methods for research, diagnostic and therapeutic applications. For example, it is demonstrated herein that primary tumors can precondition lymph nodes for tumor metastasis by inducing lymphangiogenesis in draining and distal lymph nodes, thereby facilitating the appearance of metastatic tumors. As such, one embodiment of the present invention provides the determination of risk of a subject for developing tumor metastasis by identifying lymphangiogenesis in lymph nodes. In some embodiments, the present invention provides methods and compositions for diagnosing diseases related to integrin α4β1 related to lymphagiogenesis. In some embodiments, the present invention provides for therapies for inhibiting the development of new lymphatic vessels, and for inhibiting tumor cell dissemination through the lymphatics.

In one embodiment nanoparticles find use in assays of the present invention. A nanoparticle is a small or microscopic particle. At the small end of the size range, nanoparticles are often referred to as clusters. Nanospheres, nanorods, and nanocups are examples of nanoparticle shapes. The present invention is not limited by any particular shape or size of nanoparticles, indeed all shapes and sizes are contemplated for use with applications, diagnostics and therapeutics as described herein. Metal, dielectric, and semiconductor nanoparticles are known, as well as hybrid structures (e.g., core-shell nanoparticles). Examples of nanoparticles include, but are not limited to, quantum dots, liposomes, lipid complexes, dendrimers, metal particles (e.g. gold, silver, iron oxide, copper, etc.), viral based nanoparticles, silicon nanopowder, nanodiamonds, nanocrystals, and the like (Polymeric Biomaterials, 2002, Ed. S. Dumitriu; incorporated herein by reference in its entirety).

In one embodiment, the present invention provides methods and compositions for in vitro assays comprising nanoparticles, for example, immunoassays to measure integrin α4β1 on lymphatic vessels in tumors and lymph nodes. Assays include, but are not limited to, enzyme linked immunosorbent assays, immunohistochemical, immunocytochemical, in situ hybridization, and the like. In some embodiments, results from such assays find use in predicting the risk of tumor metastasis in a subject. In some embodiments, results from said assays are used to diagnosis cancers of the lymph system. In some embodiments, results from said assays are used to diagnosis tumor metastasis.

In one embodiment, the present invention provides methods and compositions comprising nanoparticles that are modified (e.g., with reactive groups) to bind ligands (e.g., small molecules, peptides, proteins, antibodies, etc.) to integrin α4β1 for use, for example, in in vivo diagnostic (e.g., MRI, PET, optical imaging, etc.) applications. For example, nanoparticles that are loaded with small molecules, peptides, proteins, antibodies, etc. to integrin α4β1 are applied (e.g., orally, injection, etc.) to a subject. The loaded nanoparticles bind to integrin α4β1 in vivo and such binding is visualized, for example, by diagnostic instruments such as MRI and PET imaging instrumentation. In some embodiments, a diagnosis is furnished to a subject based on the outcome of such a diagnostic application (e.g., risk of tumor metastasis, cancer, etc.).

In one embodiment, the present invention provides methods and compositions comprising nanoparticles that are modified (e.g., with reactive groups) to bind ligands (e.g., small molecules, peptides, proteins, antibodies, etc.) to integrin α4β1 for use as therapeutics (e.g., drug delivery) for inhibiting the development of new lymphatic vessels, and for inhibiting tumor cell dissemination through the lymphatics. In some embodiments, the therapeutic compound (e.g., drug, small molecule, peptide, etc.) for binding integrin α4β1 for inhibiting the development of new lymphatic vessels, and for inhibiting tumor cell dissemination through the lymphatics is complexed (e.g., non-covalently bound) with nanoparticles. For example, nanospheres that are modified or complexed with antibodies, small molecules, drugs, peptides, etc. and the like for inhibiting integrin α4β1 are applied (e.g., orally, by injection, transdermally, by implantation, by inhalation, etc.) to a subject to prevent tumor metastasis through the lymph system. Nanoparticles that find use in therapeutics as described include metal nanoparticles (e.g., gold, etc.), lipid-based nanoparticles (e.g., DOPE, DOTMA, DOTAP, etc.), polymer based nanoparticles (e.g. poly(alkycyanocacrylates, etc.) (Vauthier et al., 2003, Adv. Drug Del. Rev. 55:519; incorporated herein by reference in its entirety), and biological nanoparticles (e.g., viral particles such as retrovirus, HSV-1, adenovirus, adenoassociated virus, etc.) (Thomas et al., 2003, Nature 4:346; incorporated herein by reference in its entirety).

IV. Experimental and Results

The following examples are provided in order to demonstrate and further illustrate certain preferred embodiments and aspects of the present invention and are not to be construed as limiting the scope thereof.

The following reagents and protocols were utilized in experiments: Anti-Lyve-1 antibodies (rabbit anti-human and anti-mouse) were purchased from Research Diagnostic Incorporation (Flanders, N.J.). Rat anti-mouse CD31, rat anti-mouse integrin α5β1 (5H10), rat anti-mouse beta 5 and biotinylated anti-beta 3 were from BD Bioscience (San Diego, Calif.). Mouse anti-human CD31, mouse anti-human α4β1 (HP1/2), rabbit anti-beta 5, mouse anti-human cytokeratin, rat anti-mouse VCAM-1, and mouse anti-human Fibronectin (TEV-1) were from Chemicon international (Temecula, Calif.). Goat anti-integrin alpha 4 (sc-6590) is from Santa Cruz Biotechnology (Santa Cruz, Calif.). PS2 (anti-murine α4β1) hybridoma was a gift from Biogen-Idec, Cambridge, Mass. JBS5 (mouse anti-human α5β1) was a gift from Chemicon. P1F6 (mouse anti-human αvβ5), and LM609 (mouse anti-human αvβ3) were from David Cheresh, UCSD Moores UCSD Cancer Center, San Diego, Calif. Isotype controls (IgG2a and IgG2b) were purchased from BD Bioscience. Antibodies for cell sorting and cytometry (anti-CD34, -α4β1, -α5β1, -αvβ3 and -αvβ5 were from BD pharmingen (San Diego, Calif.). For anti-Prox-1 immunostaining of cryosections of lymph nodes, sections were blocked with purified rat anti-mouse CD16/CD32 (murine Fc block) from Becton Dickinson Pharmingen 10 μg/ml, 30 min at room temperature. The anti-Prox1 antibody (Chemicon International) was used at the dilution 1:500 for 2 hours at room temperature.

Statistical analysis were performed with a two-tailed indirect Student's t-test.

Example 1

Murine Lymphangioma Model

C57Bl/6 mice from Jackson Labs, 6 weeks of age, were injected twice at 15 day intervals in the intraperitoneal cavity with 200 μL of Incomplete Freud's adjuvant diluted 1:1 in PBS. Mice were sacrificed after 4 weeks. The tumors were then removed from the diaphragm and upper surface of both lobes of the liver, embedded in OCT, frozen and sectioned for immunohistological analysis (Mancardi et al., 1999, Exp. Cell Res. 246:368).

Example 2

Subcutaneous Tumor Model

Murine Lewis Lung Carcinoma cells (LLC) and Human colon carcinoma cells (HT29) were cultured in DMEM medium supplemented with 1-glutamine and 10% fetal bovine serum. Tumor cells ($5 \times 10^6$) in 200 μl PBS were injected subcutaneously into 6 week-old nude mice (nu/nu), n=10. Animals bearing LLC tumors were treated with anti-α4β1 antibodies three times per week for two weeks, beginning either 1 day or 14 days after tumor cell inoculation.

Example 3

Murine Lymphangiogenesis and Angiogenesis Assays

Lymphangiogenesis and angiogenesis assays in MATRIGEL were performed as described (Eliceiri et al, 1999, Mol. Cell 4:915) by injecting subcutaneously into wild-type C57Bl/6 mice (n=5) 400 μL of cold MATRIGEL containing 400 ng of bFGF, VEGF-A, or VEGF-C (R&D Systems, Minneapolis, Minn.). Mice were then injected twice at day1 and day3 with 200 μl of blocking anti-α4β1 (PS2) or anti-α5β1 (5H10) antibodies, or isotype control antibody. After 7 days, MATRIGEL plugs were removed, embedded in OCT, frozen and sectioned. Thin sections (5 μm) were immunostained with anti-CD31 antibodies.

In other experiments, MATRIGEL containing 400 ng/ml VEGF-C was injected subcutaneously into Tie2Cre+a4flox/flox (n=4), Tie2Cre+a4flox/+(n=2) or Tie2Cre−a4fl/fl (n=4) mice.

Example 4

Immunofluorescence Microscopy

Frozen tissue sections were frozen 1 hour at room temperature with various antibodies followed with corresponding secondary antibody conjugated with Alexa Fluor 488 or 594 (Invitrogen, Carlsbad, Calif.). Sections were mounted in Dako Cytomation fluorescent mounting medium (Dako Corporation, Carpinteria, Calif.). All thin sections were photographed at ×200 magnification. Experiments were done five to ten times.

For quantification, vessel numbers, tumor foci or pixel number in 10 microscopic fields per cryosection (per animal)

Example 5

Cytometry Cell Sorting and FACS Analysis

FACS analysis was performed at the UCSD Cancer Center core faculty. Cell sorting was performed on dermal Human Microvascular Endothelial Cells (HMVEC, Clonetics, San Diego, Calif.) using negative selection of the CD34 positive cells using PE-conjugated mouse anti-human CD34 (BD Pharmingen). Integrin expression was studied on the CD34 negative, LYVE-1 positive lymphatic microvascular endothelial cells (LEC).

Example 6

Cell Culture and Adhesion Assay

Lymphatic endothelial cells (LEC) and HMVEC were grown in endothelial growth medium containing 2% fetal bovine serum (Clonetics, San Diego, Calif.). Cell adhesion assays on ECM substrates were done as previously described (Bakre et al., 2002, Nat. Med. 8:995) using 25 µg/mL final concentration of anti-$\alpha v \beta 3$ (LM609), anti-$\alpha v \beta 5$ (PIF6), anti-$\alpha 4 \beta 1$ (HP1/2) and anti-$\alpha 5 \beta 1$ (JBS5) blocking antibodies.

Example 7

Cell Culture and In Vitro Cell Analysis

Podoplanin positive lymphatic endothelial cells from Cambrex (LEC) were grown in lymphatic endothelial growth medium containing 2% fetal bovine serum (Cambrex). Integrin $\alpha 4 \beta 1$ and Lyve-1 expression was analyzed on lymphatic endothelial cells (LEC). Cell adhesion assays on the H95 fraction of CS-1 fibronectin were performed as previously described using 25 µg/ml final concentration of isotype matched control antibodies (cIgG) and anti-$\alpha 4 \beta 1$ (HP1/2) function blocking antibodies. All in vitro assays were performed three times with triplicate samples per group. The mean number of cells adhering +/−s.e.m. for the entire treatment group in each experiment was determined.

Example 8

MATRIGEL Tube Formation

MATRIGEL (BD Biosciences) was added to the wells of an 8 well chamber slide in a volume of 150 µl and allowed to solidify at 37° C. for 30 min. After the MATRIGEL solidified, LEC ($5 \times 10^4$ cells) were added in 300 µl of media EGM-2 without serum containing 50 ng/mL of VEGF-C. 25 µg/mL final concentration of anti-$\alpha 4 \beta 1$ (HP1/2) and anti-$\alpha 5 \beta 1$ (JBS5) were added 30 min prior to addition of the cells. The cells were incubated at 37° C. with humidified 95% air/5% CO2 for 24 h.

Example 9

Stimulation of Lymph Node Lymphangiogenesis with VEGF-C

C57BL/6 mice were injected subcutaneously with 350 µl of ice-cold saline or VEGF-C-containing Matrigel (1 µg/ml) proximal to the inguinal lymph node. In parallel, $5 \times 10^5$ LLC cells were injected dorsally near the inguinal or brachial lymph nodes. Mice were sacrificed after 1, 7 and 14 days. Mice with stimulated inguinal nodes were also sacrificed after 21 days. Inguinal, brachial and mesenteric lymph nodes were removed and embedded in OCT for cryosectioning and immunohistochemistry.

Example 10

Local and Systemic Delivery of Anti-$\alpha 4 \beta 1$ or Anti-VEGFR3 Antibodies C57BL/6 mice were inoculated dorsally with $5 \times 10^5$ LLC cells. Intradermal injections of 50 µl of saline or 50 µg of sterile, endotoxin-free anti-mouse $\alpha 4 \beta 1$ (PS2), anti-VEGF-R3, or isotype control were performed every 3 days starting on day 1 (7 injections per mice, 5 mice per group). Alternatively, mice were systemically treated every third day for 14 days with 200 µg/mouse of the same antibodies (n=8). Mice were sacrificed after 21 days and tumors, inguinal, brachial and mesenteric lymph nodes were removed and embedded in OCT for
cryosectioning and histological analysis.

Example 11

Experimental Footpad Injection Metastasis Studies

Inguinal lymph node lymphangiogenesis was stimulated by injecting mice intradermally above the left inguinal lymph node with 50 µl of saline or VEGF-C (200 ng per mice) every day for 7 days. Mice were inoculated with $10^6$ RFP-LLC cells in a volume of 150 µl in the left footpad. Twenty four hours later, mice were sacrificed. Inguinal, brachial and mesenteric lymph nodes were removed and embedded in OCT for cryosectioning and immunofluorescence. RFP-tumor cell and Lyve-1+pixels were quantified on 5 different sections per lymph node.

Example 12

Lymph Node Lymphangiogenesis Time Course

A time course of tumor and lymph node lymphangiogenesis and metastasis was performed from 1-21 days (LLC, n=4) or 1-7 weeks after tumor cell inoculation
(pancreatic carcinoma, n=6). The tumors were then removed, as were inguinal, brachial and mesenteric lymph nodes, embedded in OCT, frozen and sectioned for immunohistological analysis of lymphatic vessel density (by Lyve-1 immunuostaining), for blood vessel density (by CD31 immunodetection) and for metastases by cytokeratin immunodetection. At least five microscopic fields per tissue section were analyzed for quantification studies. Primary tumor volume and mass was also determined.

Example 13

Endothelial Cell Specific Integrin $\alpha 4$ Deletion Mutant

C57BL/6×129 mice homozygous for the floxed $\alpha 4$ allele were crossed to C57BL/6 mice expressing Cre under the control of the Tie2 promoter (Cg-Tg Tek-cre 12Flv/J from Jackson Labs mice to generate Tie2Cre+$\alpha 4$ flox/+mice). Mating of these Tie2Cre+$\alpha 4$ flox/+mice with $\alpha 4$ flox/flox mice yielded Tie2Cre+$\alpha 4$ flox/flox, Tie2Cre+$\alpha 4$ flox/+, Tie2Cre–α4 flox/flox mice and Tie2Cre–α4 flox/+mice. Genotyping was performed by PCR on mouse tail DNA using the primers
(F) 5'-CGGGATCAGAAAGAATCCAAA-3'(SEQ ID NO:36) and
(R) 5'-CTGGCATGGGGTTAAAATTG-3' (SEQ ID NO:37)
to yield a 180 bp product in wild-type mice and
a 250 bp product in floxed mice. Primers
(F) 5'-CCACCTGGTGTATGAAAGC-3'(SEQ ID NO:38) and
(R) 5'-CTGGCATGGGGTTAAAATTG-3' (SEQ ID NO:39)
were used to identify the excised α4
flox allele. Expression of Cre was evaluated by PCR amplification of tail DNA with the primers
(F) 5'GCGGTCTGGCAGTAAAAACTATC3' (SEQ ID NO:40) and
(R) 5'GTGAAACAGCATTGCTGTCACTT3' (SEQ ID NO:41) to yield a 100 bp product.

Figure 2:
FIG. 2: Lymphatic vessel expression of integrin in murine tumor and normal tissues. Quantification of the percentage of integrin positive lymphatic vessels. $*p<0.001$.×200 magnification of cryosections.

To determine which integrins are expressed on lymphatic vessels, immunostained cryosections of human breast cancer (dysplastic carcinoma in situ, DCIS), normal human breast, spontaneous mouse breast carcinomas and normal mouse breast were immunostained with antibodies directed against LYVE-1 and integrins αvβ3, α4β1, α5β1, and αvβ5. In both human (FIG. 1) and mouse (FIG. 2) breast carcinomas, lymphatic vessels expressed only integrins α4β1 and αvβ5 (FIGS. 1-2). More than 80% of the lymphatic vessels in tumors expressed integrin α4β1, while none of the lymphatic vessels in normal tissues expressed this integrin. In contrast, normal and tumor tissues expressed equal levels of integrin αvβ5. As such, integrin α4β1, but not other integrins, is strongly upregulated in human and mouse tumor lymphatic vessels (FIG. 1-2).

Figure 3:
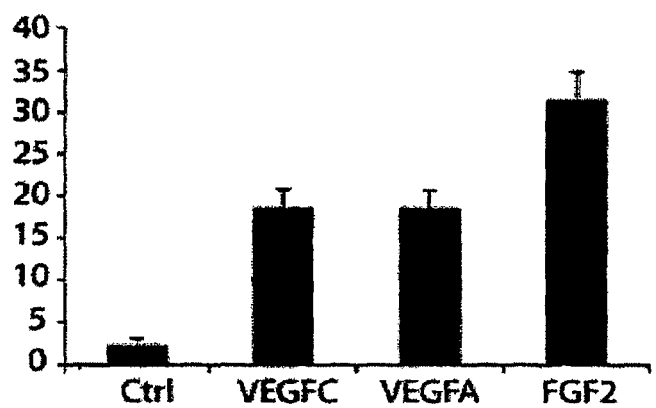
FIG. 3: Expression of $\alpha4\beta1$ on LEC on growth factor stimulated lymphatic endothelium. Quantification of the percentage of $\alpha4\beta1$ positive lymphatic vessels upon growth factor stimulation.
Figure 4:
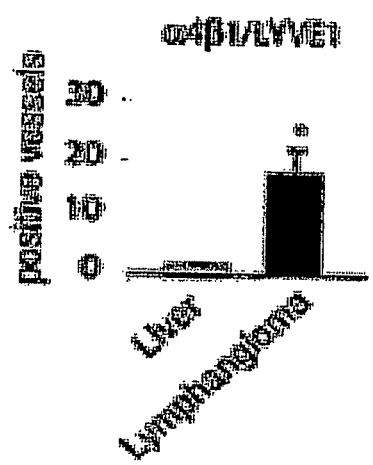
FIG. 4: Integrin $\alpha4\beta1$ expression in lymphatic endothelium in a murine model of lymphangioma. Wild type C57B1/6 were injected in the peritoneal cavity twice with a 15 days interval, with 200 μL of emulsified (1:1 with PBS) incomplete Freund's adjuvant. Cryosections of lymphangiomas were immunostained to detect integrin $\alpha4\beta1$ expression and LYVE-1. Quantification of integrin $\alpha4\beta1$/LYVE-1+ lymph nodes. Magnification ×200, $*p<0.001$.

To evaluate the regulation of integrin α4β1 in lymphangiogenesis, expression of integrin α4β1 in response to various angiogenic growth factors was examined. It was found that new lymphatic vessels invade MATRIGEL saturated with VEGF-C, VEGF-A and bFGF and that these vessels are integrin α4β1 positive (FIG. 3). In addition, it was determined that lymphatic vessels growing within lymphangiomas, which were induced by intraperitoneal injection of Incomplete Freund's adjuvant, also expressed integrin α4β1 in contrast to normal liver and other normal tissues (FIG. 4). As such, α4β1 is expressed on growing lymphatic vessels in vivo.

To examine whether integrin α4β1 regulates lymphatic endothelial cell adhesion and migration, CD34-, LYVE-1 positive lymphatic endothelial cells from primary cultures of human microvascular endothelial cells were isolated by FACS cell sorting. The purified lymphatic endothelial cells (LEC) were LYVE-1 positive (98%). In vitro cultured cells expressed integrins α4β1 and α5β1 integrins (87% and 99% positive, respectively) but poorly expressed integrins αvβ3 and αvβ5 (23% and 20% positive, respectively).

Figure 5:
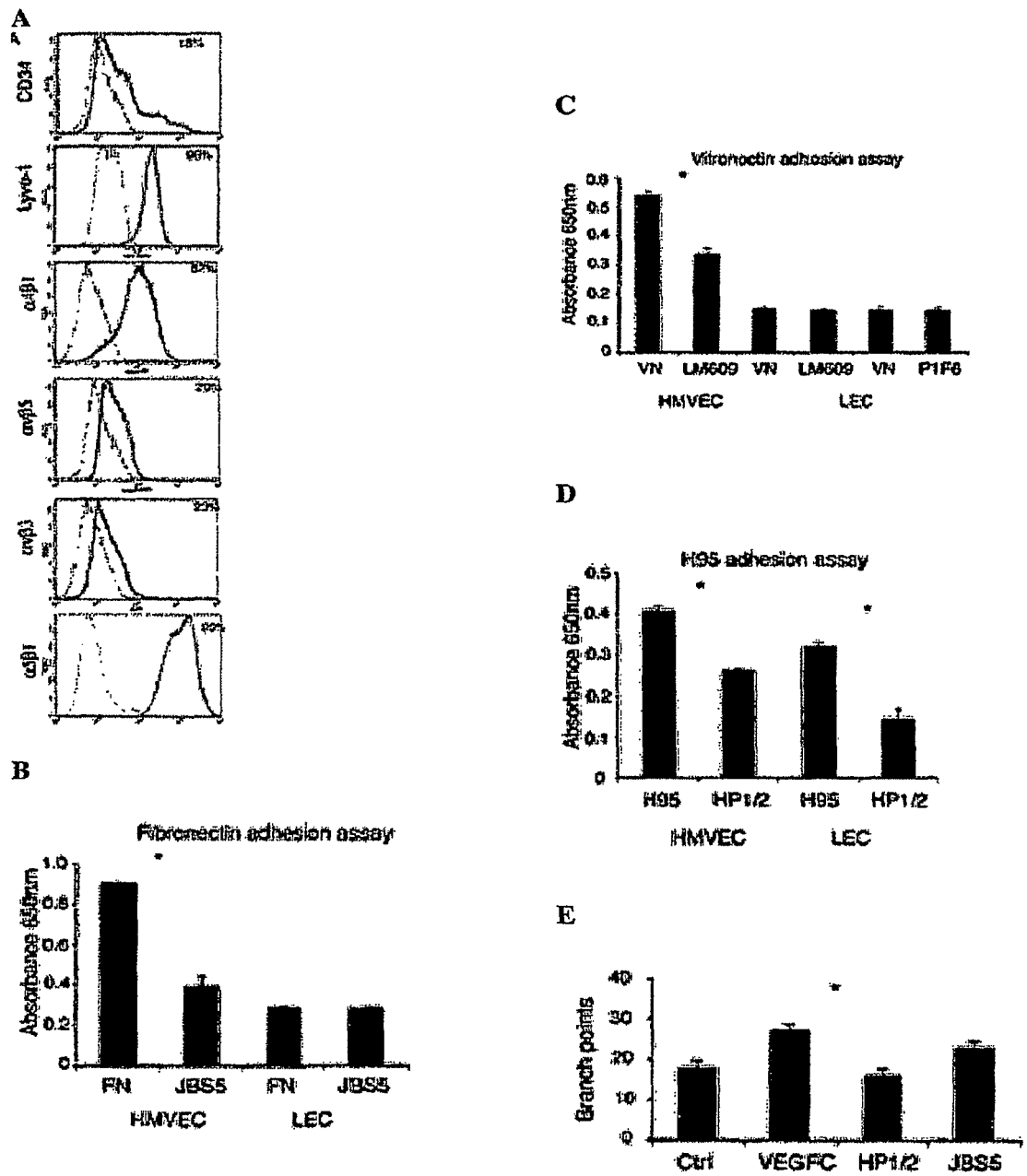
FIG. 5: Integrin expression on human LEC in vitro. A) LEC were isolated by flow cytometry cell sorting using an anti-CD34 antibody. The CD34 negative fraction has been purified and cultured. The expression of LYVE-1 was detected using a FITC-coupled secondary antibody. The expression of CD34, $\alpha v\beta3$, $\alpha4\beta1$, $\alpha5\beta1$, and $\alpha v\beta5$ were detected using fluorochrome conjugated antibodies. B-D) Adhesion of LEC to the extracellular protein matrix in the presence of blocking antibodies. B) Adhesion of integrin $\alpha5\beta1$ positive cells to fibronectin in the presence of anti-$\alpha5\beta1$ (JBS5) antibody. C) Adhesion of integrin $\alpha v\beta3$ and $\alpha v\beta5$ positive cells to vitronectin in the presence of anti-$\alpha v\beta3$ (LM609) and anti-$\alpha v\beta5$ (P1F6) antibody. D) Adhesion of integrin $\alpha4\beta1$ positive cells to CS-1 fibronectin in the presence of anti-$\alpha4\beta1$ (HP1/2) antibody. E) Inhibition of the LEC-tubes formation in growth factor reduced MATRIGEL matrix in the presence of anti-$\alpha4\beta1$ but not anti-$\alpha5\beta1$ antibody.

Experiments were performed to determine whether these integrins are functionally active (FIG. 5, B-D). The adhesive capacities of cultured endothelial cells to cultured LEC were compared. It was determined that vascular endothelial cells (VEC), but not LEC, adhere robustly to plasma fibronectin and to vitronectin in integrin α5β1- and αvβ3-dependent manners, respectively (FIG. 5 B-C). In contrast, both VEC and LEC adhered to the alternatively spliced form of fibronectin, CS-1 fibronectin, in an integrin α4β1 dependent manner (FIG. 5D). To evaluate a functional role for integrin α4β1 in lymphatic vessel invasion, the ability of LEC to invade and form tube-like structures in MATRIGEL in vitro was evaluated. It was found that LEC invaded MATRIGEL and formed tubes in the presence of VEGF-C in vitro and that this process was inhibited by function-blocking antibodies to integrin α4β1 but not to integrin α5β1 (FIG. 5E).

Figure 6:
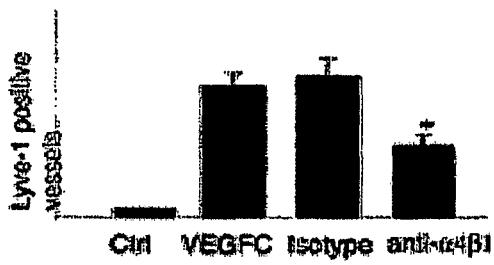
FIG. 6: Integrin $\alpha4\beta1$ regulates VEGF-C-induced lymphangiogenesis. Mice with VEGFC-containing MATRIGEL plugs were treated by intravenous injection with 200 μg anti-$\alpha4\beta1$ (A, C) or $\alpha5\beta1$ (B, D) antibodies every 3 days for one week. Quantification of lymphatic vessels (A, B) and blood vessels (C, D). ($*p<0.001$, $**p<0.005$).
Figure 6:
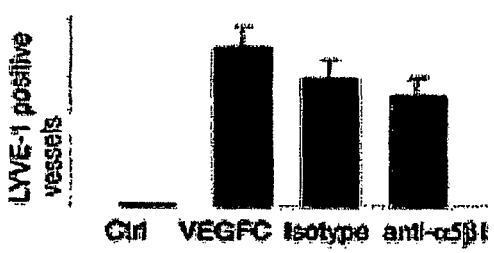
Figure 6:
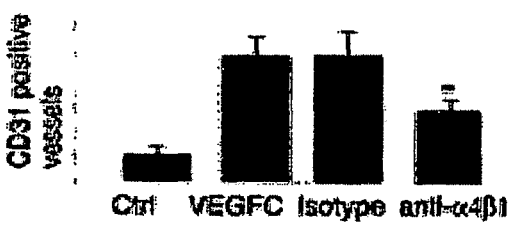
Figure 6:
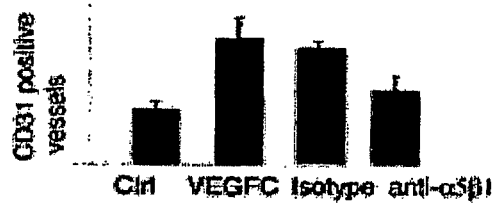

To determine whether integrin α4β1 has a functional role during lymphangiogenesis in vivo, stimulated lymphangiogenesis in mice was performed by implanting VEGF-saturated MATRIGEL (FIG. 6). Mice were then treated intravenously with function-blocking anti-α4β1 or anti-α5β1 antibodies or isotype matched control antibodies. While antagonists of integrin α5β1 had no effect on lymphangiogenesis, antagonists of integrin α4β1 completely blocked lymphangiogenesis (FIG. 6). As such, integrin α4β1 regulates lymphangiogenesis in vivo.

Figure 7:
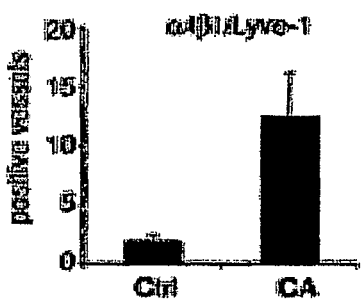
FIG. 7: Integrin $\alpha\alpha4\beta1$ regulates tumor lymphangiogenesis in colon carcinoma tumors. A, B) Treatment with anti-$\alpha4\beta1$ antibodies, but not saline inhibits lymphangiogenesis in HT29 colon carcinoma tumors.
Figure 7:
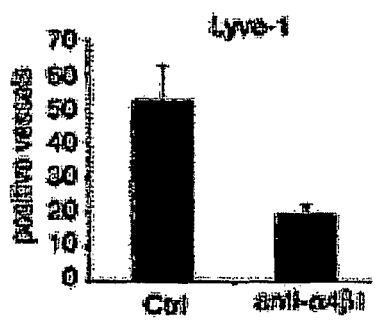
Figure 8:
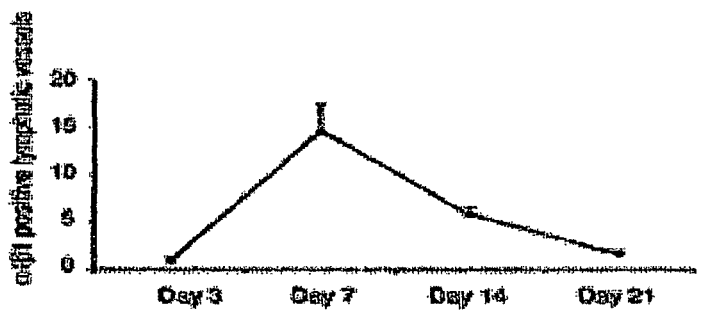
FIG. 8: Integrin $\alpha4\beta1$ regulates tumor lymphangiogenesis in lung carcinoma tumors. A) Quantification of $\alpha4\beta1$ expression on lymphatic vessels in tumors over 21 days of tumor growth. B) Quantification of tumor volume, LYVE-1 expression and CD31 expression.
Figure 8:
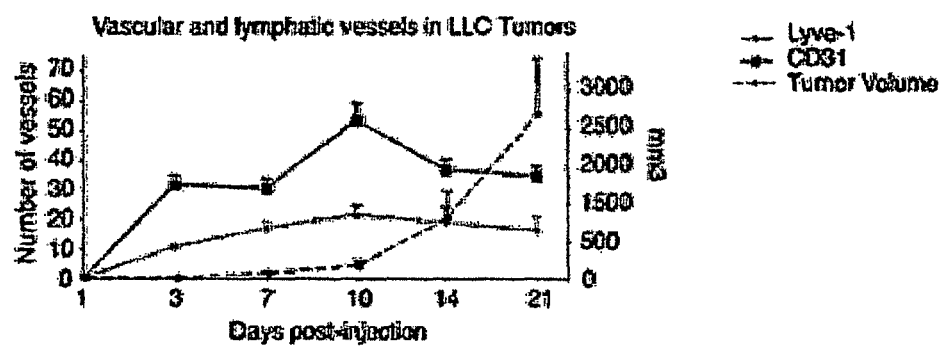

To explore the role of integrin α4β1 in tumor lymphangiogenesis, the expression of α4β1 in a mouse model of subcutaneous colon carcinoma (HT29) tumor growth (FIG. 7) was determined. It was found that α4β1 is expressed on tumor associated lymphatic vessels within HT29 colon carcinoma tumors (FIG. 7A). To study the role of α4β1 in tumor lymphangiogenesis, mice were treated with intravenous injections of function-blocking anti-α4β1 antibodies or saline (FIG. 7B). Function blocking anti-α4β1 antibodies suppressed colon carcinoma lymphangiogenesis by more 60% (FIG. 7). It was also found that antagonists of integrin α4β1 blocked Lewis lung carcinoma tumor lymphangiogenesis (FIG. 8). It was therefore determined that α4β1 regulates tumor lymphangiogenesis.

Figure 9:
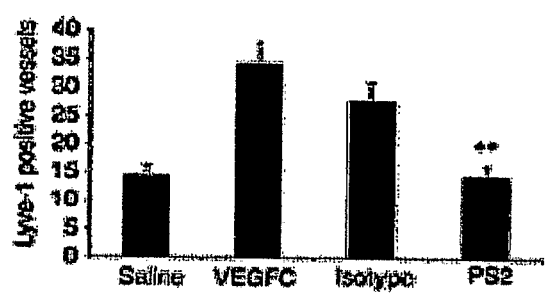
FIG. 9. Integrin $\alpha4\beta1$ regulates lymphangiogenesis in lymph nodes in response to growth factors. Quantification of LYVE-1 positive vessels in tissues from B, $**p<0.005$.

Tumor secreted factors induce proliferation of lymphatic endothelial vessels and induce expression of integrin α4β1 on these vessels. It was found that tumors and VEGF-C also induce integrin α4β1 expression and lymphangiogenesis in lymph nodes. Lymph nodes proximal to implanted MATRIGEL containing VEGF-C expanded dramatically in size and exhibited a significant increase in lymphatic vessel density (FIG. 9). In animals treated with inhibitors of integrin α4β1, however, the lymph nodes remained normal in size and exhibited normal lymphatic vessel density.

Figure 10:
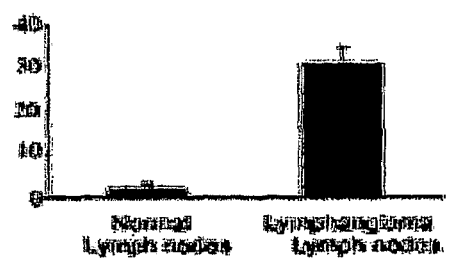
FIG. 10. Integrin $\alpha4\beta1$ expression on lymphatic vessels in lymph nodes from animals bearing Lewis lung carcinomas. Quantification of $\alpha4\beta1$ lymphatic vessel expression in lymph nodes from normal and tumor bearing animals.
Figure 11:
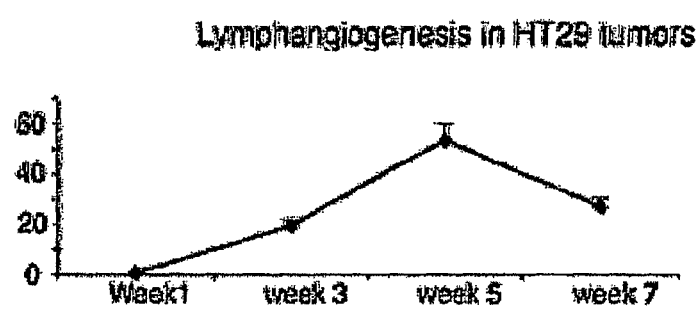
FIG. 11. Integrin $\alpha4\beta1$ expression on lymphatic vessels in lymph nodes from animals bearing HT29 colon carcinomas. Quantification of the number of $\alpha4\beta1$ positive lymphatic vessels in the lymph nodes over a seven week period.
Figure 12:
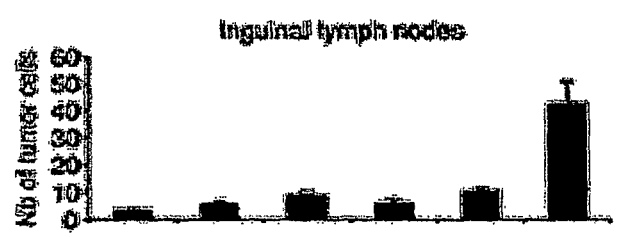
FIG. 12. Lewis lung carcinomas metastasize to sentinel and distal lymph nodes. LLC metastasis were detected by cytokeratin immunostaining in Inguinal (A), Brachial (B), and Mesenteric (C) lymph nodes after 21 days of primary tumor growth.
Figure 12:
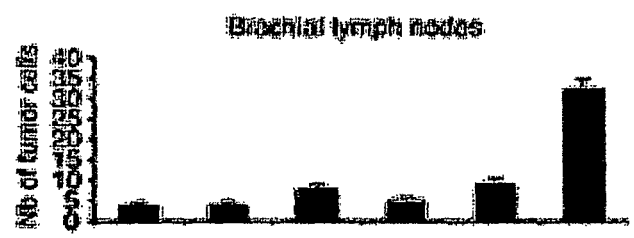
Figure 12:
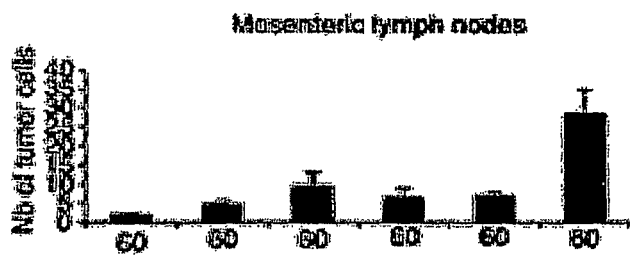
Figure 13:
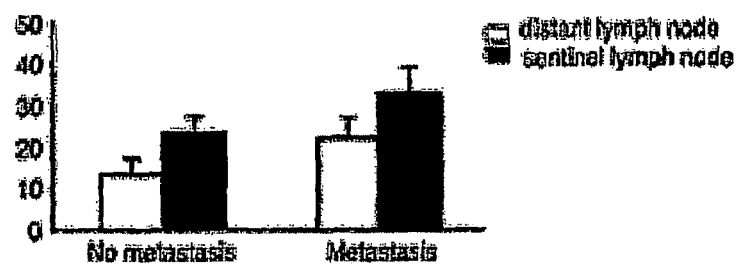
FIG. 13. Lymphangiogenesis in lymph nodes is associated with metastasis of spontaneous breast carcinomas. Quantification of lymphatic vessels in lymph nodes from animals with and without lymph node metastases.
Figure 14:
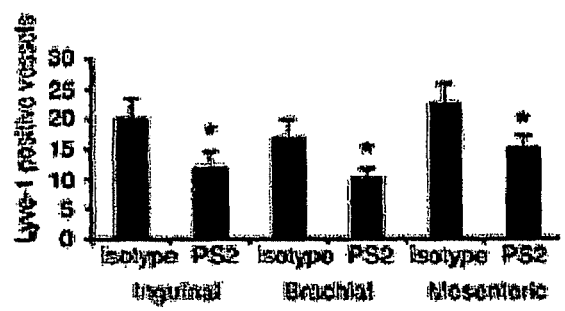
FIG. 14. Integrin α4β1 promotes lymph node lymphangiogenesis and subsequent tumor metastasis to lymph nodes. A) Quantification of lymphangiogenesis in sentinel and distant lymph nodes from mice treated with anti-α4β1 (PS2) or control (isotype) antibodies. B) Quantification of the cytokeratin tumor foci in sentinel and distant lymph nodes from mice treated with anti-α4β1 (PS2) or control (isotype) antibodies.
Figure 14:
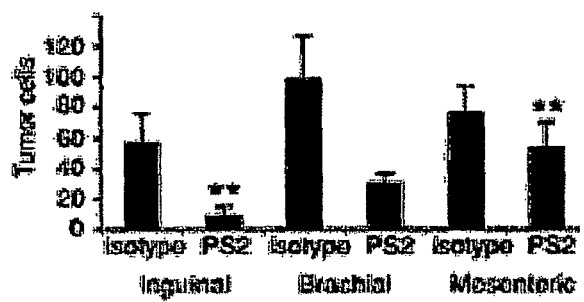

Lymph nodes proximal to and distal to implanted Lewis lung carcinomas (FIG. 10), HT29 colon carcinomas (FIG. 11) and spontaneous breast carcinomas (FIG. 13) also exhibited an increase in lymphatic vessel density and integrin α4β1 expression. This enhanced lymphangiogenesis was associated with tumor metastasis to lymph nodes (FIG. 12-13). In fact, antagonists of integrin α4β1 suppressed lymph node lymphangiogenesis as well lymph node metastasis, indicating that integrin α4β1 regulation of lymphangiogenesis within lymph nodes and primary tumors promotes lymphangiogenesis and subsequent spread of tumors by the lymphatics (FIG. 14).

Primary tumors can precondition lymph nodes for tumor metastasis by inducing lymphangiogenesis in draining and distal lymph nodes, thereby facilitating the appearance of metastatic lesions.

Figure 22:
FIG. 22. Lymphangiogenesis in Lewis lung carcinoma tumors and lymph nodes. A) Mean+/−s.e.m. Prox-1+pixels/ field in d1-21 inguinal lymph nodes from animals with subcutaneous Lewis lung carcinomas. *p<001. B) Mean+/−s.e.m. tumor volume (cm3), CD31+ and Lyve-1+ vessels/ field in d1-21 LLC primary tumors. C) Mean+/−s.e.m. Lyve-1+ lymphatic vessels/field from d. *p=0.01. D) Quantification of mean+/−s.e.m. RFP+pixels/field (indicative of metastases) in d1, d21 and d28 lung (solid line) and lymph nodes (dotted line). Note that metastases appear in lymph nodes on d21 before they appear in lung on d28 (arrowhead). *p<0.001.
Figure 22:
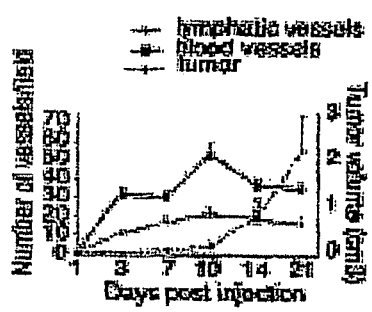
Figure 22:
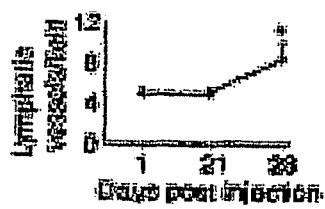
Figure 22:
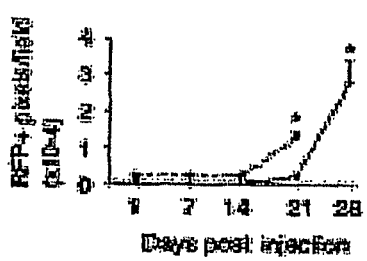
Figure 23:
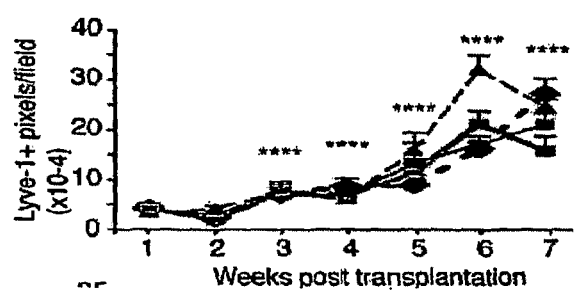
FIG. 23. Lymph node lymphangiogenesis precedes lymph node metastases in a murine model of orthotopic pancreas tumor transplantation. (A-B) Mean+/−s.e.m. Lyve-1+ (A) and RFP+ (B) pixels/field in the pancreatic (grey line), inguinal (thick dotted line), brachial (thin dotted line), and mesenteric (solid line) lymph nodes. *p<0.05.
Figure 23:
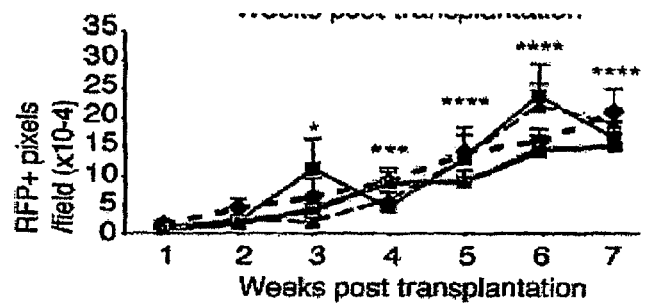
Figure 24:
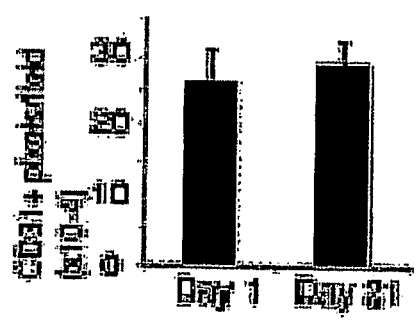
FIG. 24. No blood vessel angiogenesis in lymph nodes of LLC bearing animals. Mean+/−s.e.m. CD31+pixels/field from a. No statistical difference was observed between d1 and d21.

To determine whether lymph node lymphangiogenesis could promote tumor metastasis, Lyve-1+19 and Prox-1+20 lymphatic vessels and cytokeratin+tumor metastases in the draining and distal lymph nodes of mice bearing a syngeneic Lewis lung carcinoma (LLC) tumor (FIGS. 18B-C, FIG. 22A) were quantified. Tumors were implanted dorsally proximal to the inguinal lymph node. The density of lymphatic vessels in draining inguinal and distal brachial and mesenteric lymph nodes increased as early as 3 days post tumor implantation, ultimately showing a ten-fold density increase by 21 days. In contrast, tumor metastases to lymph nodes were only detected until after 21 days of tumor growth and metastases to lungs only after 28 days (FIGS. 18A-B, FIGS. 22B-D). Thus, lymphangiogenesis in lymph nodes preceded the appearance of tumor metastases to draining and distal lymph nodes by two weeks. A similar pattern of lymphangiogenesis preceding metastasis was observed in lymph nodes of animals bearing xenogeneic, orthotopic pancreatic carcinoma (FIGS. 23A-B). Lymphangiogenesis in other tissues, such as lung, was not observed until after the appearance of metastases on day 28 (FIG. 22C-D). Importantly, no similar increase in blood vessel density was observed in lymph nodes after tumor cell implantation (FIG. 24). These results indicate that primary tumors precondition lymph nodes to undergo lymphangiogenesis, but not hemangiogenesis, prior to the arrival of tumor metastases, suggesting that tumors establish a pre-metastatic niche within lymph nodes.

Figure 18:
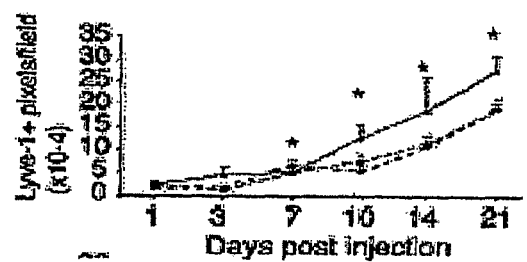
FIG. 18. Lymph node lymphangiogenesis precedes lymph node metastases A) Mean+/−s.e.m. Lyve-1+pixels/field in the inguinal (tumor draining, thin dotted line), brachial (thick dotted line), and mesenteric (solid line) lymph nodes. *p<0.05. B) Mean+/−s.e.m. tumor foci/field in inguinal (thin dotted line), brachial (thick dotted line) and mesenteric (solid line) lymph nodes. *p<0.005. C) Mean+/−s.e.m. Lyve-1+ pixels/field in draining (inguinal) and distal (brachial) lymph nodes from animals stimulated with systemic injections of VEGF-C or local injections of MATRIGEL saturated with saline or VEGF-C. *p=0.001 and *p=0.0003 for systemic and local injections, respectively.
Figure 18:
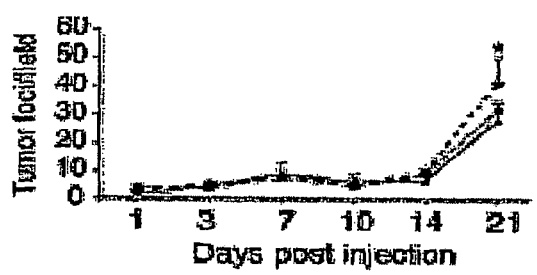
Figure 18:
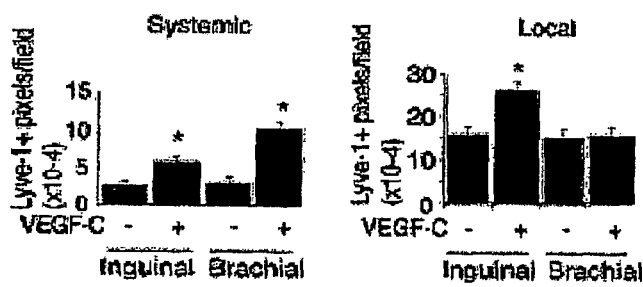
Figure 25:
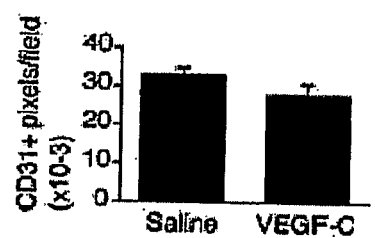
FIG. 25. Effect of systemic versus local delivery of VEGF-C on distal lymph nodes. Mean CD31+pixels/field+/− s.e.m. No statistical difference was observed between saline and VEGF-C treatments.
Figure 26:
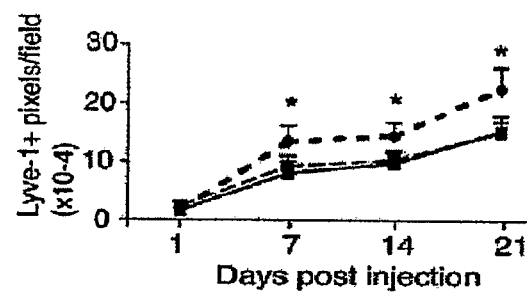
FIG. 26. Local VEGF-C stimulation increases lymphatic vessel density and accelerates tumor metastases: d1-21 time course. (A-B) Mice were inoculated on d1 with LLC cells and injected with VEGF-C or saline containing Matrigel plugs next to the inguinal lymph node. A) Mean+/−s.e.m. Lyve-1+ pixels/field in VEGF-C stimulated inguinal (thick dotted line) and brachial (thin dotted line) lymph nodes and saline stimulated inguinal (solid line) lymph node. *p<0.05. Mean+/− s.e.m. cytokeratin positive pixels in lymph nodes as in b. *p<0.001.
Figure 26:
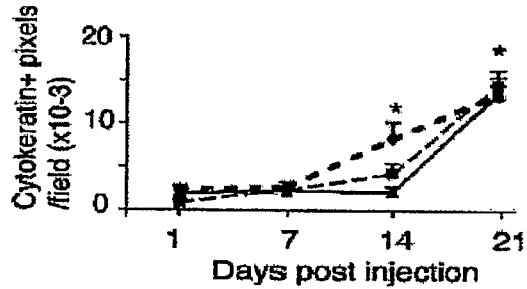

On the basis of the findings that both tumor draining and distant lymph nodes exhibit lymphangiogenesis, it was postulated that tumor-derived circulating factors, such as the lyrnphangiogenesis-promoting factor VEGF-C, induces widespread lymph node lymphangiogenesis. As such, lymphatic vessel density in lymph nodes of normal mice after systemic or local injections of VEGF-C was compared. Widespread lymph node lymphangiogenesis resulted from systemic VEGF-C injections (FIG. 18C), while local injections proximal to a single lymph node specifically affected this and not other nodes (FIG. 18D). Importantly, VEGF-C stimulation of lymph nodes had no significant effect on blood vessels within lymph nodes (FIG. 25). These results suggest that tumor-derived factors, such as VEGF-C, promotes either local or widespread lymph node lymphangiogenesis.

Figure 19:
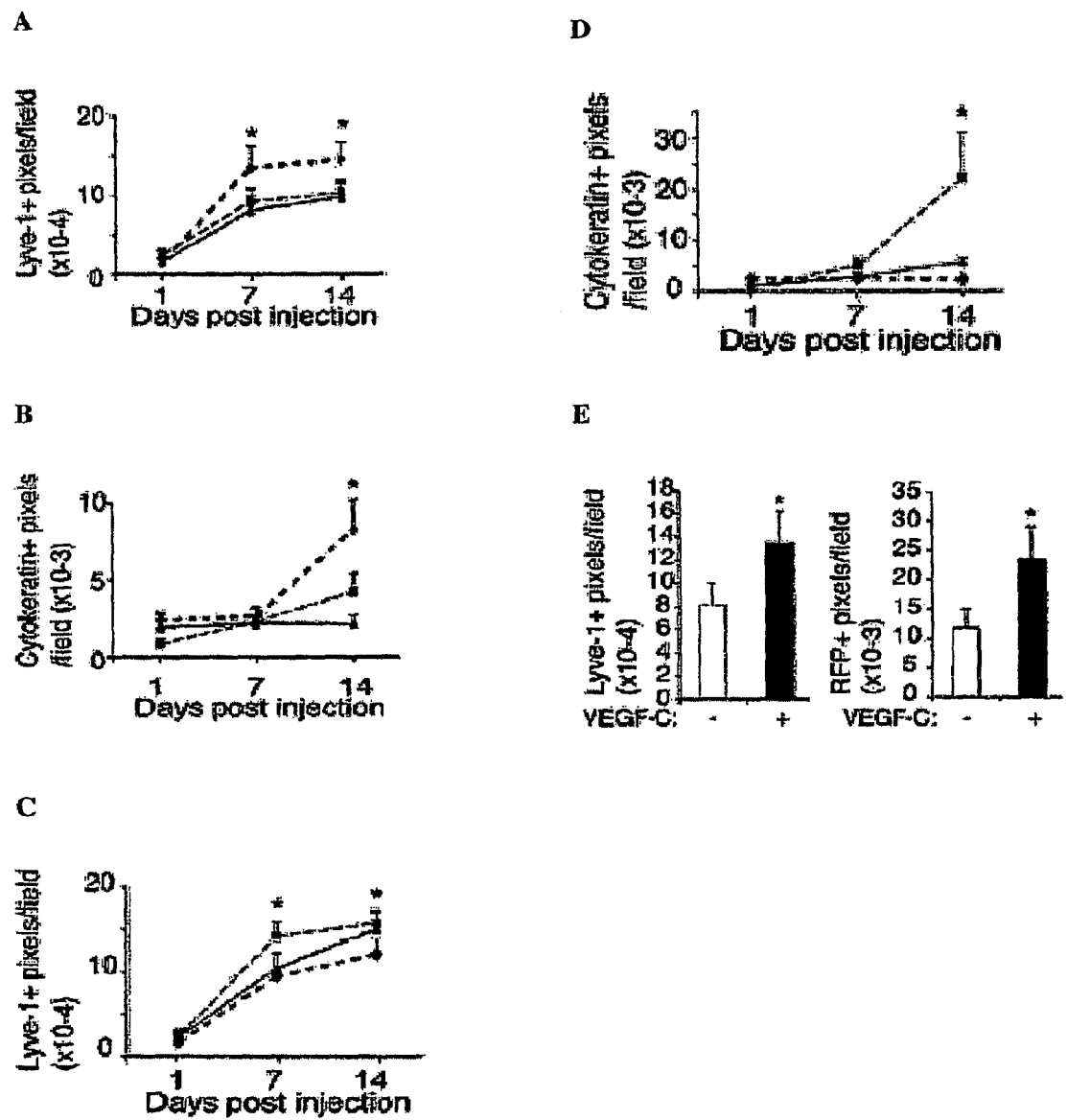
FIG. 19: Stimulation of lymphangiogenesis accelerates tumor metastases (A-E) Mice were inoculated on d1 with LLC cells and concurrently injected with VEGF-C containing MATRIGEL adjacent to the inguinal (A-B) or brachial (C-D) lymph nodes. Mean+/−s.e.m. (A,C) Lyve-1+pixels/field and (B,D) cytokeratin positive pixels/field in V-EGF-C stimulated inguinal (thick dotted line) and brachial (thin dotted line) lymph nodes and in unstimulated inguinal (solid line) lymph nodes. * p<0.005 (A), *p<0.001 (B), *p=0.05 (C), *p=0.003 (D). E) Mice were stimulated by daily intradermal injections of VEGF-C proximal to the left inguinal node for 7 days, then injected with RFP-LLC cells into the left footpad on d8. Lymph nodes were removed 24 h later. Mean+/−s.e.m. Lyve-1+pixels/field (left) and RFP+pixels/field in inguinal lymph nodes. *p=0.04 and *p=0.04, respectively.
Figure 27:
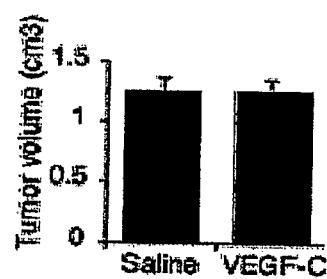
FIG. 27. No effect of local VEGF-C stimulation on primary tumor growth. Quantification of tumor volume (cm3) after 21 days from mice inoculated on d1 with LLC cells and injected with saline or VEGF-C containing Matrigel next to the inguinal lymph node. No statistical difference was observed between tumors from mice injected with saline and VEGF-C Matrigel.

To determine whether lymph node lymphangiogenesis potentiates tumor metastasis, the draining (inguinal) lymph nodes of tumor-bearing mice were stimulated by local injection of saline or VEGF-C for one week immediately after tumor cell inoculation. Local VEGF-C stimulation significantly increased lymphatic vessel density and induced tumor metastases by 14 days rather than the 21 days observed for saline treated animals (FIGS. 19A-B, FIG. 26A-B). Significantly, local VEGF-C stimulation had no effect on lymphangiogenesis and metastasis to other lymph nodes or on primary tumor growth (FIG. 27). Similar results were obtained when lymph nodes were pretreated for one week with local VEGF-C injections prior to tumor cell inoculation. In fact, stimulation of a distant lymph node (the brachial node) by VEGF-C selectively enhanced lymphangiogenesis and accelerated metastasis by one week without affecting the rate of lymphangiogenesis or metastasis to inguinal or mesenteric nodes (FIG. 19C-D). These studies indicate that lymphangiogenesis in lymph nodes significantly enhances tumor metastasis to those specific lymph nodes.

Figure 28:
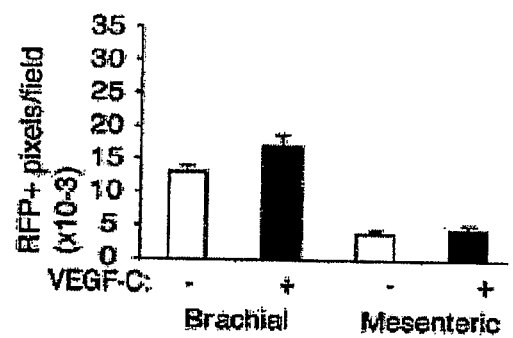
FIG. 28. Effect of VEGF-C stimulation on tumor cell homing to brachial and mesenteric lymph nodes. Mice were stimulated by intradermal injections of saline or VEGF-C proximal to the inguinal node daily for 7 days. On d8, mice were injected with LLC-RFP tumor cells into the footpad. Mean+/−s.e.m. RFP+pixels/field in lymph nodes from saline (white bars) and VEGF-C (black bars) stimulated mice. No statistical difference was observed between the saline and VEGF-C stimulated nodes.
Figure 29:
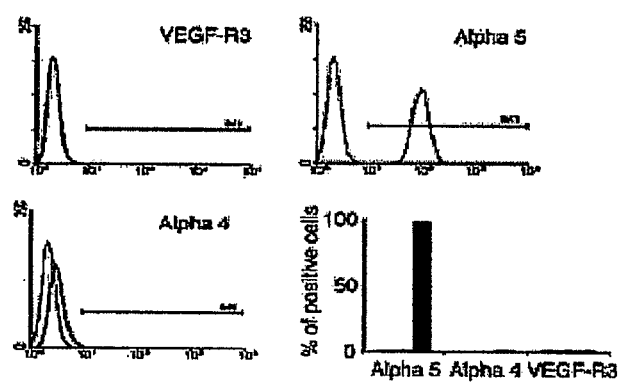
FIG. 29. Analysis of LLC cell expression of integrin α4 and VEGF-R3. A) Expression of VEGF-R3, integrins α5β1 and α4β1 (black lines) on LLC cells was evaluated by flow cytometry. Grey lines depict binding of isotype matched control IgG. While 100% of cells express integrin α5β1, none express α4β1 or VEGF-R3. B) Transwell migration of LLC cells in the presence or absence of serum or VEGF-C at 10, 100 or 500 ng/ml.
Figure 29:
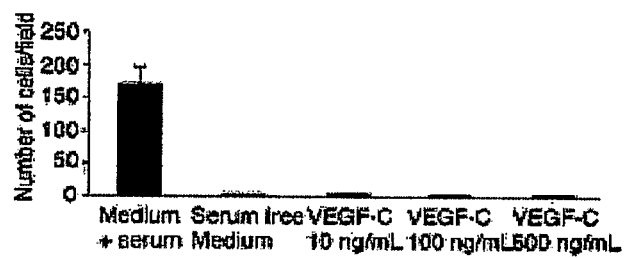

To determine whether lymph node lymphangiogenesis is sufficient to promote tumor metastasis, inguinal lymph nodes of normal, non-tumor bearing mice were stimulated with intradermal injections of VEGF-C or saline proximal to the node. After one week, red fluorescent LLC tumor cells (RFP-LLC) was injected directly into the lymphatic vasculature in footpads of stimulated mice and harvested lymph nodes 24 h later. VEGF-C stimulation significantly induced lymphangiogenesis and strongly enhanced tumor cell retention in the stimulated inguinal lymph node (FIG. 19E), but not in unstimulated brachial or mesenteric lymph nodes (FIG. 28). These studies suggest that increased lymphatic vessel surface area or VEGF-C activation of lymphatic endothelium in lymph nodes provides increased sites for tumor cell adhesion and/or extravasation into the lymph nodes. As LLC cells do not express the VEGF-R3 receptor for VEGF-C and do not migrate in response to VEGF-C (FIG. 29A-B), these studies indicate that VEGF-C preconditions lymph nodes for tumor metastasis by initiating lymphangiogenesis in the lymph nodes prior to the arrival of tumor cells.

To determine whether lymphangiogenesis is necessary for tumor metastasis to lymph nodes, we sought to identify inhibitors of lymphangiogenesis. One family of cell surface receptors that plays a functional role in blood angiogenesis is the integrin family of extracellular matrix adhesion proteins.

Figure 31:
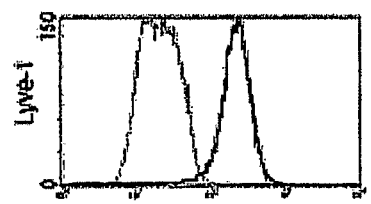
FIG. 31. Integrin expression and function on human LEC in vitro. Expression of A) LYVE-1 and B) integrin α4β1 (black lines) and isotype matched control IgG (gray lines) on purified human lymphatic endothelial cells (LEC) was evaluated by flow cytometry. (C) Adhesion of human LEC to the α4β1 ligand H95 fragment of CS-1 fibronectin in the absence (medium) or presence of anti-α4β1 function-blocking or isotype matched control (cIgG) antibodies. *p=0.008.
Figure 31:
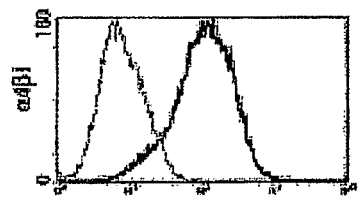
Figure 31:
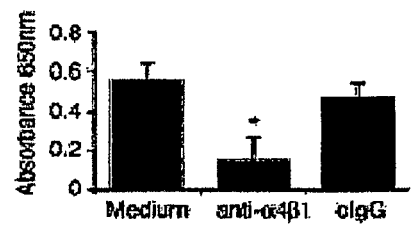

To determine if integrins regulate lymphangiogenesis, the expression patterns of integrins in lymphatic vessels was examined, and it was found that the fibronectin-binding integrin α4β1 was expressed on human and murine breast carcinoma lymphatic vessels, but not on normal lymphatic vessels. This integrin was also expressed on lymphatic endothelium in VEGF-C stimulated lymph nodes but not normal lymph nodes, on lymphatic endothelium in VEGF-C saturated MATRIGEL in vivo and on lymphatic endothelial cells in vitro (FIG. 31). Expression of α4β1 integrin was coincident with expression of three independent markers of lymphatic endothelium: Lyve-1, Prox-1 and podoplanin.

Figure 20:
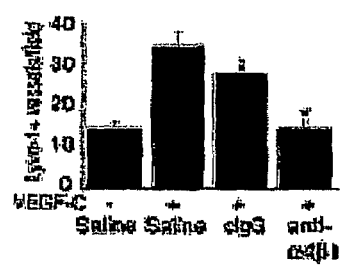
FIG. 20. Integrin α4β1 regulates lymph node lymphangiogenesis. A) Mean Lyve-1+vessels/field+/−s.e.m. (n=5). *p=0.001. B) Mean+/−s.e.m. Lyve-1+pixels/field in tumors from d (n=10). *p=0.0007 C) Mean+/−s.e.m. Lyve-1+pixels/ 200× field in lymph nodes from d (n=10). *p=0.006.
Figure 20:
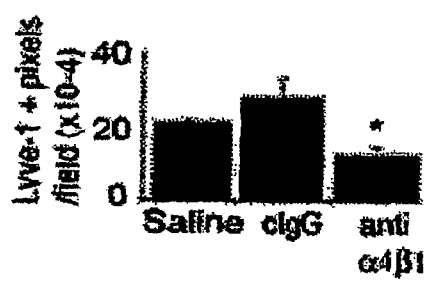
Figure 20:
Figure 30:
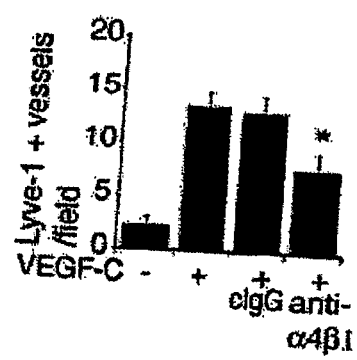
FIG. 30. Lymphatic vessel integrin α4β1 expression and function. A) The mean numbers of Lyve-1+lymphatic vessels per 200× microscopic field+/−s.e.m were quantified. *p=0.002. Bars indicate 50 μm. B) The mean numbers of CD31+ blood vessels per 200× microscopic field+/−s.e.m were quantified. No significant difference was observed between treatments.
Figure 30:
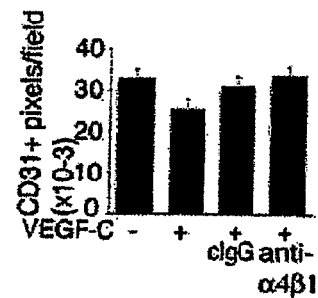

Systemic administration of antagonists of integrin α4β1 blocked VEGF-C stimulated lymphangiogenesis in MATRIGEL (FIG. 30A) and in lymph nodes (FIG. 20A). These antagonists had no effect on blood vessels in lymph nodes (FIG. 30B). These antagonists also inhibited lymphangiogenesis in LLC primary tumors and adjacent draining lymph nodes (FIGS. 20B-C).

Figure 32:
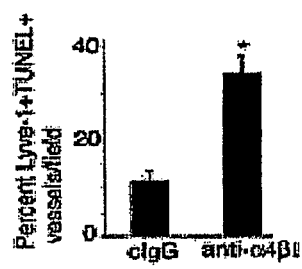
FIG. 32. Integrin α4β1 antagonists induce apoptosis of lymphatic endothelial cells. A) Quantification of the percent of TUNEL+Lyve1+vessels/field from each treatment group (n-S). Asterisk indicates p<0.001. B) Quantification of TUNEL+Lyve1+vessels/field in VEGF-C stimulated lymph nodes treated with saline, isotype matched control antibodies (anti-CD1) and anti-α4β1 antibodies (n=5). *p<0.001.
Figure 32:
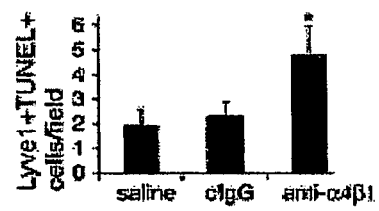
Figure 33:
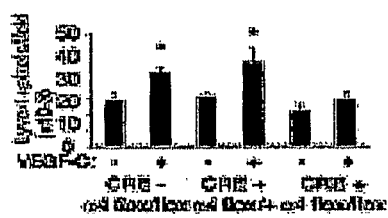
FIG. 33. Genetic loss of integrin α4β1 suppresses lymphangiogenesis. (A-B) Quantification of mean+/−s.e.m. Lyve1+pixels/field from saline (−) and VEGF-C (+) stimulated animals in Matrigel (A) or lymph nodes (B). *p<0.01. C) Genomic PCR analysis of Tie2Cre+α4flox/flox, Tie2Cre+ α4flox/+ and Tie2Cre−α4flox/flox mice for Cre-recombinase gene (100 bp), intact integrin α4 gene (180 bp), floxed α4 allele (280 bp) and excised α4 allele (600 bp). D) Western blotting of Cre-recombinase (38 kD) and beta-actin (42 kD) in lysates of lung from Tie2Cre+α4flox/flox and Tie2Cre− α4flox/flox mice.
Figure 33:
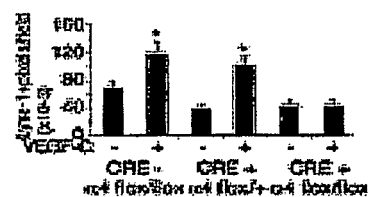
Figure 33:
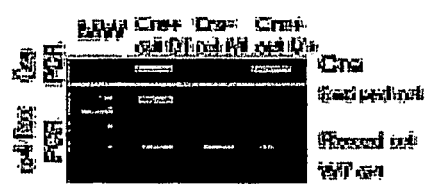
Figure 33:
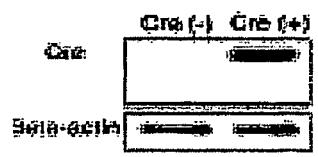
Figure 34:
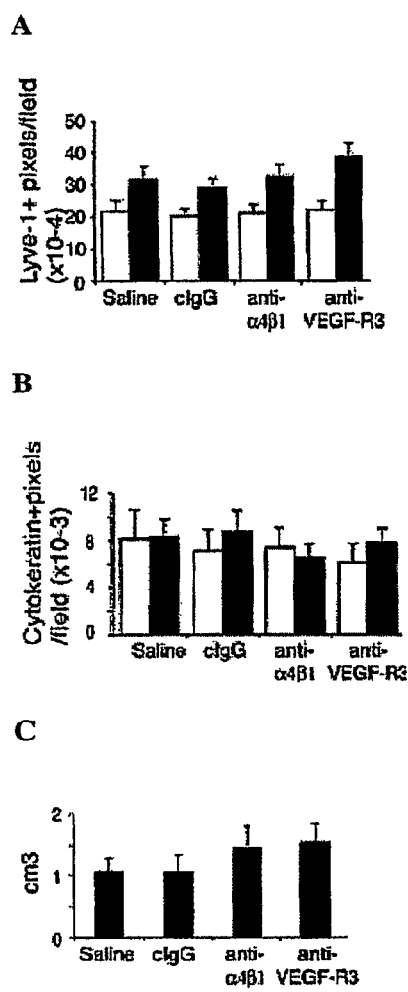
FIG. 34. Effect of local antagonists of lymphangiogenesis on tumor metastasis to distant lymph nodes. (A-B) Mice inoculated on d1 with LLC cells were treated d1-21 with intradermal injections proximal to the inguinal node of anti-α4β1, anti-VEGF-R3 or isotype matched control (cIgG) antibodies. A) Mean+/−s.e.m. Lyve-1+pixels/field in d21 lymph nodes (n=5). White bars, brachial nodes and black bars, mesenteric nodes. *p=0.01. B) Mean+/−s.e.m. cytokeratin positive pixels in d21 lymph nodes (n=5). White bars, brachial nodes and black bars, mesenteric nodes. *p<0.001. C) Mean+/−s.e.m. (cm3) primary tumor volume on d21.

To assess the functional role of α4β1 in lymphangiogenesis, the effect of a single dose of integrin α4β1 function-blocking or control antibody on lymphatic endothelial cell survival in VEGF-C stimulated lymph node and MATRIGEL was examined. It was found that antagonists of this integrin significantly blocked lymphatic endothelial cell survival in vivo within 48 hours after administration (FIG. 32A-B). In support of these findings, lymphangiogenesis in subcutaneous MATRIGEL plugs and lymph nodes was suppressed in mice lacking expression of integrin α4β1 in lymphatic endothelial cells (Tie2Cre αfl/fl mice27) (FIG. 33). Thus, integrin α4β1 plays a key role in regulating lymph node lymphangiogenesis. Although integrin α4β1 was recently shown to promote blood vessel angiogenesis, it is herein demonstrated that the role of integrin α4β1 in lymph node lymphangiogenesis is independent of its role in blood vessel angiogenesis.

Figure 21:
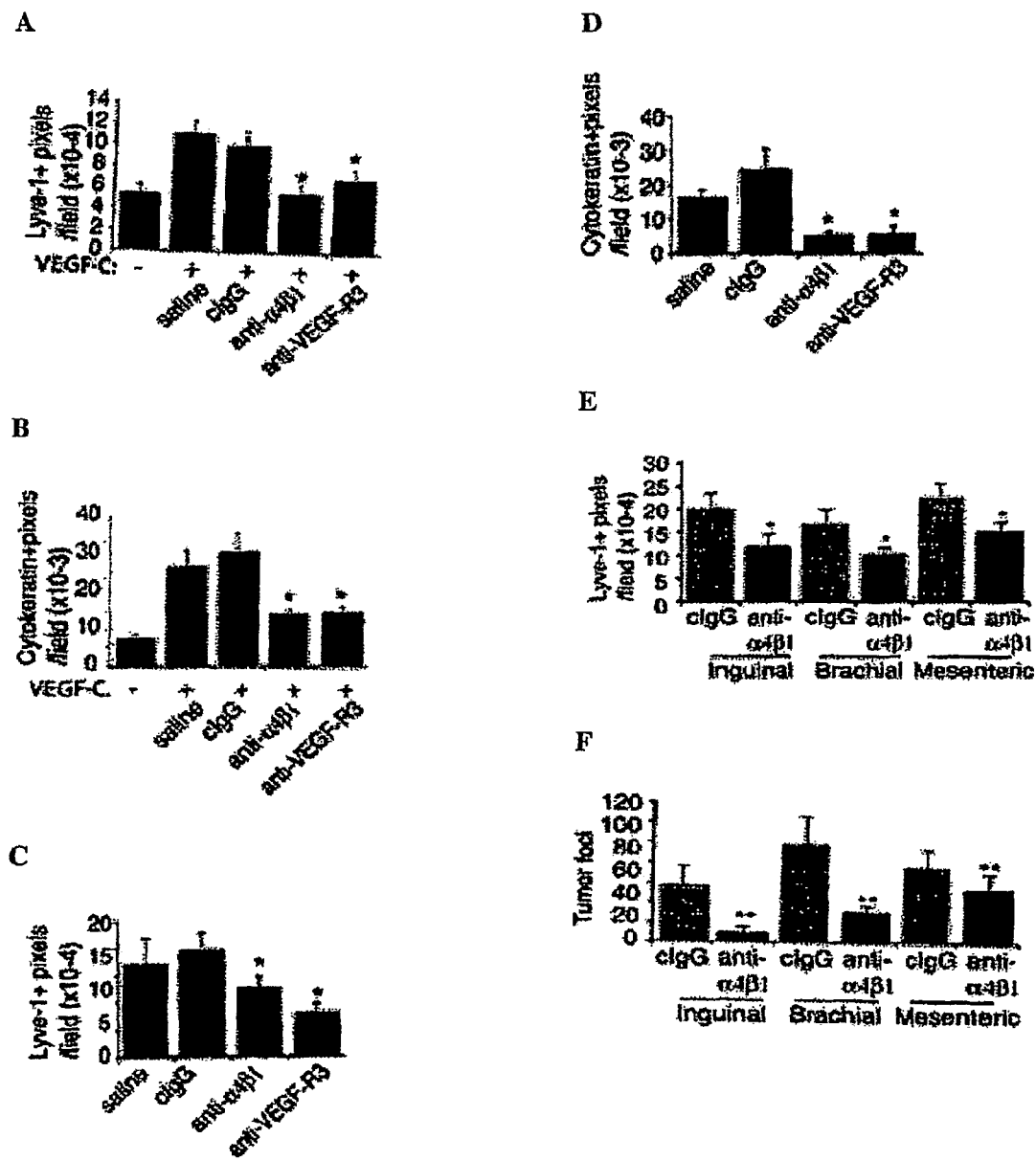
FIG. 21. Lymph node lymphangiogenesis is necessary for tumor metastasis. (A-B) Mice were inoculated with LLC cells and injected with saline or VEGF-C containing MATRIGEL proximal to the inguinal lymph node on d1 and treated from d1-14 with systemic injections of anti-α4β1, anti-VEGF-R3 or isotype-matched control (cIgG) antibodies. A) Mean+/−s.e.m. Lyve-1+pixels/field in inguinal lymph nodes. *P<0.005. B) Mean+/−s.e.m. cytokeratin positive pixels in lymph nodes. *p<0.001. (C-D) Mice inoculated on d1 with LLC cells were treated d1-21 with intradermal injections proximal to the inguinal node of anti-α4β1, anti-VEGF-R3 or isotype-matched control (cIgG) antibodies. C) Mean+/−s.e.m. Lyve-1+pixels/field in d21 inguinal lymph nodes (n=5). *p=0.01. D) Mean+/−s.e.m. cytokeratin positive pixels in d21 inguinal lymph nodes (n=5). *p<0.001. (E-F) Mice were inoculated with LLC cells and treated systemically with anti-α4β1 or isotype-matched control (cIgG) antibodies. E) Mean+/−s.e.m. Lyve-1+pixels/field from g.*p=0.03. F) Mean+/−s.e.m. cytokeratin positive tumor foci from (g). *p<0.05.
Figure 35:
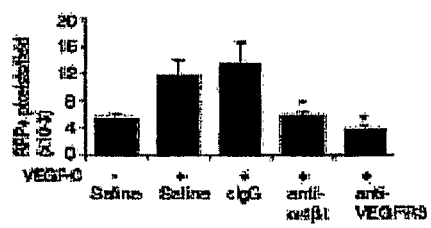
FIG. 35. Suppression of experimental tumor metastasis by inhibitors of lymphangiogenesis. Mice were stimulated by intradermal injections of saline, VEGF-C, VEGFC+anti-α4β1, VEGF-C+anti-VEGFR3 and VEGF-C+cIgG proximal to the inguinal node daily for 7 days. On d8, mice were injected with LLC-RFP tumor cells into the footpad. Mean+/−s.e.m. RFP+pixels/field in inguinal lymph nodes. *p=0.01 for anti-α4β1 and 0.002 for anti-VEGF-R3.

To determine if lymph node lymphangiogenesis is required for tumor metastasis, lymph node lymphangiogenesis in tumor-bearing animals was enhanced by VEGF-C injections as in FIG. 19A-B and systemically treated animals with function-blocking antibody antagonists of either integrin α4β1 or VEGF-R3 (FIG. 21A-B). Both antagonists suppressed VEGF-C enhanced lymphangiogenesis and tumor metastasis to the inguinal lymph node, indicating that both antagonists regulate VEGF-C-induced lymph node lymphangiogenesis and subsequent metastasis. Although LLC cells are both integrin α4β1 and VEGF-R3 negative (FIG. 29A), systemic administration of these inhibitors could potentially affect lymph node lymphangiogenesis indirectly by impacting the primary tumor. Therefore, mice bearing LLC tumors were treated with local, intradermal injections of either α4β1 or VEGF-R3 antagonists proximal to a single inguinal lymph node. Local administration of these antagonists suppressed lymphangiogenesis and blocked tumor metastasis to the treated, but not to the untreated, lymph nodes and had no effect on primary tumor growth (FIGS. 21C-D, FIGS. 34A-C). It was also observed that systemic administration of integrin α4β1 antagonists suppressed lymph node lymphangiogenesis and tumor metastasis to the draining (inguinal) and distal (brachial and mesenteric) lymph nodes (FIGS. 21E-F). It was also observed that antagonists of α4β1 and VEGF-R3 suppress lymphangiogenesis and subsequent tumor cell retention when tumor cells are injected into footpads of mice with VEGF-C stimulated lymph nodes (FIG. 35). These results indicate that lymph node lymphangiogenesis is necessary for tumor metastasis to draining and distal lymph nodes.

All publications and patents mentioned in the above specification are herein incorporated by reference. Various modifications and variations of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the art, are intended to be within the scope of the present invention.

We claim:

1. A method for inhibiting lymphangiogenesis in lymph node tissue, comprising:
   a) providing:
      i) lymph node tissue; and
      ii) an an-integrin alpha4beta1 antibody or an antigen-binding fragment of said antibody that interferes with specific binding of integrin alpha4beta1 to an integrin alpha4beta1 ligand; and
   b) contacting said lymph node tissue with said an-integrin alpha4beta1 antibody or an antigen-binding fragment of said antibody under conditions such that
      i) specific binding of said integrin alpha4beta1 to said integrin alpha4beta1 ligand is inhibited,
      ii) lymphangiogenesis in said lymph node tissue is inhibited, and
      iii) angiogenesis in said lymph node tissue is not altered.

2. The method of claim 1, wherein said tissue is in a subject.

3. The method of claim 2, wherein said subject has a pathological condition associated with lymphangiogenesis.

4. The method of claim 3, wherein said tissue comprises one or more of a tumor-proximal lymph node and a tumor-distal lymph node.

5. The method of claim 1, wherein said inhibiting lymphangiogenesis in said tissue comprises reducing the number of Lyve-1 positive vessels in said tissue.

* * * * *